(12) United States Patent
Yang (10) Patent No.: US 9,585,855 B2
(45) Date of Patent: *Mar. 7, 2017

(54) USE OF NITRATED LIPIDS FOR TREATMENT OF SIDE EFFECTS OF TOXIC MEDICAL THERAPIES

(71) Applicant: UNIVERSITY OF UTAH RESEARCH FOUNDATION, Salt Lake City, UT (US)

(72) Inventor: Tianxin Yang, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 121 days.

This patent is subject to a terminal disclaimer.

(21) Appl. No.: 14/205,108

(22) Filed: Mar. 11, 2014

(65) Prior Publication Data

US 2014/0256815 A1 Sep. 11, 2014

Related U.S. Application Data

(63) Continuation of application No. 12/996,848, filed as application No. PCT/US2009/047825 on Jun. 18, 2009, now Pat. No. 8,686,038.

(60) Provisional application No. 61/073,945, filed on Jun. 19, 2008.

(51) Int. Cl.
A61K 31/201 (2006.01)

(52) U.S. Cl.
CPC .................. A61K 31/201 (2013.01)

(58) Field of Classification Search
None
See application file for complete search history.

(56) References Cited

U.S. PATENT DOCUMENTS

| | | |
|---|---|---|
| 3,578,687 A | 5/1971 | Larkin et al. |
| 3,819,561 A | 6/1974 | Bruenner |
| 3,917,660 A | 11/1975 | Sasaki et al. |
| 4,599,430 A | 7/1986 | Milberger et al. |
| 5,412,137 A | 5/1995 | Prashad et al. |
| 5,741,211 A | 4/1998 | Renirie et al. |
| 6,187,747 B1 | 2/2001 | Singh et al. |
| 6,262,029 B1 | 7/2001 | Press et al. |
| 6,346,231 B1 | 2/2002 | Opheim |
| 6,376,688 B1 | 4/2002 | Ferrante et al. |
| 6,407,075 B1 | 6/2002 | Scott et al. ............... 514/34 |
| 6,410,802 B1 | 6/2002 | Dasseux et al. |
| 6,531,150 B1 | 3/2003 | Sunohara et al. |
| 6,652,879 B2 | 11/2003 | Opheim |
| 6,924,309 B2 | 8/2005 | Ferrante et al. |
| 6,998,395 B2 | 2/2006 | Jackson et al. |
| 7,312,191 B2 | 12/2007 | Rose et al. |
| 7,452,907 B2 | 11/2008 | Cheng et al. |
| 7,776,916 B2 | 8/2010 | Freeman et al. |
| 7,977,315 B2 | 7/2011 | Rose et al. |
| 8,309,526 B2 | 11/2012 | Freeman et al. |
| 8,324,277 B2 | 12/2012 | Freeman |
| 8,563,609 B2 | 10/2013 | Miller |
| 8,686,038 B2 | 4/2014 | Yang |
| 8,686,167 B2 | 4/2014 | Miller |
| 8,735,449 B2 | 5/2014 | Freeman |
| 8,933,255 B2 | 1/2015 | Miller |
| 8,937,194 B2 | 1/2015 | Miller |
| 9,006,473 B2 | 4/2015 | Freeman et al. |
| 9,066,902 B2 | 6/2015 | Freeman et al. |
| 9,186,408 B2 | 11/2015 | Freeman et al. |
| 9,192,600 B2 | 11/2015 | Yang |
| 9,271,952 B2 | 3/2016 | Cushing |
| 9,308,189 B2 | 4/2016 | Miller |
| 2001/0037598 A1 | 11/2001 | Suppes et al. |
| 2002/0128510 A1 | 9/2002 | Durley et al. |
| 2003/0078299 A1 | 4/2003 | Ferrante et al. |
| 2004/0006248 A1 | 1/2004 | Paiocchi et al. |
| 2004/0092590 A1 | 5/2004 | Arterburn et al. |
| 2004/0147599 A1 | 7/2004 | Gagnon et al. ............... 514/517 |
| 2004/0176451 A1 | 9/2004 | Tamai et al. |
| 2004/0254240 A1 | 12/2004 | Ferrante et al. |
| 2005/0136103 A1 | 6/2005 | Ben-Sasson et al. |
| 2005/0232981 A1 | 10/2005 | Ben-Sasson |
| 2006/0018874 A1 | 1/2006 | Radhakrishnan et al. |
| 2006/0063953 A1 | 3/2006 | Maurizio et al. |
| 2006/0100278 A1 | 5/2006 | Cooper et al. |
| 2006/0241088 A1 | 10/2006 | Arterburn et al. |
| 2007/0232579 A1 | 10/2007 | Freeman et al. |
| 2007/0275893 A1 | 11/2007 | Quay |

(Continued)

FOREIGN PATENT DOCUMENTS

| | | |
|---|---|---|
| EP | 1407767 A1 | 4/2004 |
| EP | 1772149 A1 | 4/2007 |

(Continued)

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
'Fatty Acids' in www.elmhurst.edu/vchm/vchembook/551fattyacids.html (retrieved from the internet Jan. 21, 2016).*
Kunin discloses in Clinical Infectious Diseases 18(1), pp. 1-10 (1994).*
Meyer et al. in New England Journal of Medicine 2007;357:1316-25.*
Glauser et al. in Pediatric Nephrology 1(4):615-22 (1987) (Abstract).*
Escudier et al. discloses in The Lancet, 370:2103-2111 (2007).*
Shaner et al. in Pesticide Biotransformation in Plants and Microorganisms (Hall, J. et al.); ACS Symposium Series, American Chemical Society: Washington, DC, 2000.*
Metabolite definition in https//www.nlm.nih.gov/medlineplus/ency/article/002258.htm (retrieved from the internet Jan. 21, 2016).*
Diabetic ketoacidosis in www.mayoclinic.org/diseases-conditions/diabetic-ketoacidosis/basics/treatment/con-20026470 (retrieved from the internet Jan. 21, 2016).*

(Continued)

Primary Examiner — Dennis Heyer
(74) Attorney, Agent, or Firm — Pepper Hamilton LLP (57) ABSTRACT

The present invention relates to methods of treating the side effects of a toxic medical therapy using nitrated lipids. In particular, the methods comprise the use of nitrated fatty acids or esters thereof to treat side effects, including organ system damage, caused by chemotherapy, radiotherapy, and the administration of other toxic agents.

5 Claims, 6 Drawing Sheets

(56) References Cited

U.S. PATENT DOCUMENTS

| | | | |
|---|---|---|---|
| 2008/0096961 A1 | 4/2008 | Serhan et al. | |
| 2009/0326070 A1 | 12/2009 | Freeman et al. | |
| 2010/0216884 A1 | 8/2010 | Freeman | |
| 2010/0286257 A1 | 11/2010 | Perricone | |
| 2010/0286271 A1 | 11/2010 | Perricone | |
| 2010/0286272 A1 | 11/2010 | Perricone | |
| 2011/0082206 A1 | 4/2011 | Miller | 514/560 |
| 2011/0196037 A1 | 8/2011 | Yang | 514/560 |
| 2011/0319325 A1 | 12/2011 | Miller | |
| 2012/0136034 A1 | 5/2012 | Freeman et al. | |
| 2013/0059912 A1 | 3/2013 | Freeman | |
| 2013/0101514 A1 | 4/2013 | Cushing | 424/9.1 |
| 2013/0210917 A1 | 8/2013 | Freeman et al. | |
| 2015/0246059 A1 | 9/2015 | Freeman et al. | |
| 2016/0151318 A1 | 6/2016 | Yang | |

FOREIGN PATENT DOCUMENTS

| | | | | |
|---|---|---|---|---|
| GB | 587992 | A | 5/1947 | |
| GB | 1407932 | A | 10/1975 | |
| GB | 62-132804 | A | 6/1987 | |
| WO | WO 01/06983 | | 2/2001 | A23L 1/29 |
| WO | WO 01/15673 | A3 | 3/2001 | |
| WO | WO 01/21575 | A1 | 3/2001 | |
| WO | WO 01/78654 | A2 | 10/2001 | |
| WO | WO 01/78719 | A1 | 10/2001 | |
| WO | WO 01/79156 | A1 | 10/2001 | |
| WO | WO 02/22559 | A2 | 3/2002 | |
| WO | WO 02/102364 | A1 | 12/2002 | |
| WO | WO 03/031399 | A1 | 4/2003 | |
| WO | WO 2005/073164 | A1 | 8/2005 | |
| WO | WO2005/110396 | * | 11/2005 | A61K 31/21 |
| WO | WO 2005/110396 | A2 | 11/2005 | |
| WO | WO 2006/055965 | A2 | 5/2006 | |
| WO | WO 2006/086727 | A2 | 8/2006 | |
| WO | WO 2007/140433 | A2 | 12/2007 | |
| WO | WO 2008/011085 | A1 | 1/2008 | |
| WO | WO 2008/103753 | A2 | 8/2008 | |
| WO | WO 2009/017802 | A9 | 2/2009 | |
| WO | WO 2009/129495 | A1 | 10/2009 | |
| WO | WO 2009/134383 | A2 | 11/2009 | |
| WO | WO 2009/149496 | A1 | 12/2009 | |
| WO | WO 2009/155439 | A2 | 12/2009 | |
| WO | WO 2010/042877 | A1 | 4/2010 | |
| WO | WO 2010/078504 | A1 | 7/2010 | |
| WO | WO 2010/129763 | A1 | 11/2010 | |
| WO | WO 2010/129777 | A1 | 11/2010 | |
| WO | WO 2011/011882 | A1 | 2/2011 | |
| WO | WO 2011/014261 | A1 | 2/2011 | |
| WO | WO 2011/098746 | A1 | 8/2011 | |

OTHER PUBLICATIONS

Doksorubitsin-Ebeve, "Instruktsiya po primeneniyu moditsinskogo primeneniyu" retrieved from internet at http://medi.ru/doc/f4509.htm on Nov. 19, 2014, pp. 1-6.
Lui, H., et al., "Nitro-oleic acid protects the mouse kidney from ischemia and reperfusion injury" Am J Physiol Renal Physiol 295(4): F492-F499 (2008).
PCT International Search Report issued in corresponding foreign application, pp. 1-4 (Nov. 27, 2014).
Baker, et al., "Fatty acid transduction of nitric oxide signaling: Multiple nitrated unsaturated fatty acid derivatives exist in human blood and urine and serve as endogenous peroxisome proliferator-activated receptor ligands" J. Biol. Chem. 280: 42464-42475 (2005).
Baker, et al., "Red cell membrane and plasma linoleic acid nitration products: Synthesis, clinical identification, and quantification" PNAS 101(32):11577-11582 (2004).
Cannon, "Annalog Design" Discovery, Fifth Edition, Chapter Nineteen in Burger's Medicinal Chemistry and Drug Discovery, Fifth Edition, vol. 1: Principles and Practice Wiley-Interscience pp. 783-802.

Cui, et al., "Nitrated fatty acids: Endogenous anti-inflammatory signaling mediators" Journal of Biological Chemistry 281(47): 35686-35698 (2006).
EPO Communication issued in corresponding foreign application, European Patent Application No. 09767748.8, 1 page (Dec. 27, 2011).
EPO Examination Report issued in corresponding foreign application, European Patent Application No. 09767748.8, pp. 1-3 (Oct. 23, 2012).
Gregory, et al., "5-HT3 receptor antagonists for the prevention of chemotherapy-induced nausea and vomiting" Drugs 55(2):173-189 (1998).
International Preliminary Report on Patentability issued in corresponding foreign application, PCT/US/09/047825, pp. 1-6 (Jan. 6, 2011).
International Search Report issued in corresponding foreign application, PCT/US09/047825, pp. 1-5 (Mar. 5, 2010).
Junping, et al., "Pharmacokinetics and antitumor effects of vincristine carried by microemulsions composed of PEG-lipid, oleic acid, vitamin E and cholesterol" International Journal of Pharmaceutics 251(1-2): 13-21 (2003).
Lee, et al., "Rosiglitazone ameliorates cisplatin-induced renal injury in mice" Nephrology, Dialysis, Transplantation 21: 2096-2105 (2006).
Li, et al., "PPARalpha ligand protects during cisplatin-induced acute renal failure by preventing inhibition of renal FAO and PDC activity" Am. J. Physiol. Renal Physiol. 286: F572-F580 (2004).
Lim, et al., "Nitrolinoleate, a nitric oxide-derived mediator of cell function: Synthesis, characterization, and vasomotor activity" PNAS 99(25):15941-15946 (2002).
Liu, et al., "Nitro-oleic acid protects the mouse kidney from ischemia and reperfusion injury" Am. J. Physiol. Renal Physiol. 295: F942-F949 (2008).
Menendez, et al., "Effects of gamma-linolenic acid and oleic acid on paclitaxel cytotoxicity in human breast cancer cells" European Journal of Cancer 37(3): 402-413 (2001).
Official Action issued in corresponding foreign application, Chinese Patent Application No. 200980127890.X, pp. 1-3 (Oct. 21, 2011).
Official Action issued in corresponding foreign application, Chinese Patent Application No. 200980127890.X, pp. 1-3 (Jul. 4, 2012).
Official Action issued in corresponding foreign application, Chinese Patent Application No. 200980127890.X, pp. 1-4 (Apr. 1, 2013).
Official Action issued in corresponding foreign application, Chinese Patent Application No. 200980127890.X, pp. 1-2 (Oct. 31, 2013).
Official Action issued in corresponding foreign application, Chinese Patent Application No. 200980127890.X, pp. 1-4 (Jun. 5, 2014).
Schopfer, et al., "Nitrolinoleic acid: An endogenous peroxisome proliferator-activated receptor gamma ligand" PNAS 102(7): 2340-2345 (2006).
Supplementary European Search Report issued in European Patent Application No. 09767748.8, pp. 1-6 (Dec. 8, 2011).
"Virtual Chembook" in www.elmhurst.edu/~chm/vchembook/551fattyacids.html (retrieved from the internet Dec. 12, 2012).
Written Opinion issued in corresponding foreign application, PCT/US09/047825, pp. 1-5 (Mar. 5, 2010).
Abud-Mendoza et al., "Treating severe systemic lupus erythematosus with rituximab. An open study," Reumatol. Clin. 2009, vol. 5, No. 4, 147-152.
Adjei et al., "A Phase I Trial of the Farnesyl Transferase Inhibitor SCH66336: Evidence for Biological and Clinical Activity," Cancer Res. Apr. 1, 2000, vol. 60, 1871-1877.
Akaike et al., "Antagonistic Action of Imidazolineoxyl N-Oxides against Endothelium-Dreived Relaxing Factor/*NO through a Radical Reaction," Biochem. 1993, vol. 32, 827-832.
Alber, "Signaling mechanisms of the Mycobacterium tuberculosis receptor Ser/Thr protein kinases," Curr. Opin. Struct. Biol. Dec. 2009, vol. 19, No. 6, 650-657.
Altschul et al., "Gapped BLAST and PSI-BLAST: a new generation of protein database search programs," Nucleic Acids Res. 1997, vol. 25, No. 17, 3389-3402.
Anand et al., "Synthesis and Evaluation of Small Libraries of Triazolylmethoxy Chalcones, Flavanones and 2-aminopyrimidines (56) References Cited

OTHER PUBLICATIONS as Inhibitors of Mycobacterial FAS-II and PknG," *Bioorganic & Medicinal Chem.* 2012, vol. 20, No. 17, 5150-5183.
Arnold et al., "Nitric oxide activates guanylate cyclase and increases guanosine 3':5'-cyclic monophosphate levels in various tissue preparations," *Proc. Natl. Acad. Sci.* 1977. vol. 74, 3203-3207.
Artim et al., "Nitro-oleic acid targets transient receptor potential (TRP) channels in capsaicin sensitive afferent nerves of rat urinary bladder," *Expt. Neurol.* 2011, vol. 232, 90-99.
Asakura et al., "Synthesis and biological evaluation of γ-fluoro-β, γ-unsaturated acids," *J. of Flourine Chem.* 2006, vol. 127, 800-808.
Baker et al., "Convergence of nitric oxide and lipid signaling: Anti-inflammatory nitro-fatty acids," *Free Radic. Biol. Med.* 2009, vol. 46, 989-1003.
Baker et al., "Nitro-fatty Acid Reaction with Glutathione and Cysteine; Kinetic Analysis of Thiol Alkylation by a Michael Addition Reaction," *J. of Biol. Chem.* Oct. 19, 2007, vol. 282, No. 42, 31085-31093.
Balazy et al., "Vicinal Nitrohydroxyeicosatrienoic Acids: Vasodilator Lipids Formed by Reaction of Nitrogen Dioxide with Arachidonic Acid," *J. Pharmacol. ExTher.* 2001, vol. 299, No. 2, 611-619.
Balazy, "Isomerization and Nitration of Arachidonic Acid by Nitrogen Dioxide," *Advances in Mass Spectrometry* 2001, vol. 15, 375-376.
Baldus et al., "Endothelial transcytosis of myeloperoxidase confers specificity to vascular ECM proteins as targets of tyrosine nitration," *J. Clin. Invest.* 2001, vol. 108, No. 12, 1759-1770.
Baldus et al., "Is NO News Bad News in Acute Respiratory Distress Syndrome," *Am. J. Respir. Crit. Care Med.* 2001, vol. 163, 308-310.
Ballini et al., "Nitroalkanes and Ethyl Glyoxalate as Common Precursors for the Preparation of both β-keto Esters and α,β-unsaturated Esters," *Tetrahedron Letters* 2004, vol. 45, 7027-7029.
Ballini et al., "Fast Diastereoselective Baylis-Hillman Reaction by Nitroalkenes: Synthesis of Di- and Triene Derivatives," *Tetrahedron* 2004, vol. 60, 4995-4999.
Ballini et al., "(Z)-7-Nitro-3-Heptene as Central Intermediate for the Synthesis of Jasmone, Methyl Jasmonate and γ-Jasmolactone," *Synthetic Communications* 1989, vol. 19, Nos. 3-4, 575-583.
Banker et al., *Modern Pharmaceutics*, Marcel Dekker, Inc. 1979, New York (TOC).
Bates et al., "Nitroalkene Fatty Acids Mediate Activation of Nrf2/ARE-Dependent and PPARγ-Dependent Transcription by Distinct Signaling Pathways and with Significantly Different Potencies," *Biochem.* 2011, vol. 50, 7765-7773.
Bates et al., "Noncatalytic Interactions between Glutathione S-Transferases and Nitroalkene Fatty Acids Modulate Nitroalkene-Mediated Activation of Peroxisomal Proliferator-Activated Receptor γ," *Biochem.* 2009, vol. 48, 4159-4169.
Batthyany et al., "Reversible Post-translational Modification of Proteins by Nitrated Fatty Acids In Vivo," *J. Biol. Chem.* Jul. 21, 2006, vol. 281, No. 29, 20450-20463.
Baumer, "Iodostarin 'Roche' in the treatment of Syphilis," *Deutsche Medizinische Wochenschrift* 1913, vol. 39, 1361 (case abstract) (1 page).
Beckman et al., "Apparent hydroxyl radical production by peroxynitrite. Implications for endothelial injury from nitric oxide and superoxide," *Proc. Natl. Acad. Sci.* 1990, vol. 87, 1620-1624.
Bell-Parikh et al., "Biosynthesis of 15-deoxy-$\Delta^{12, 14}$-PGJ2 and the ligation of PPARγ," *J. Clin. Invest.* 2003, vol. 112, No. 6, 945-955.
Bennett et al., *Cecil Textbook of Medicine* 1996, 20$^{th}$ Ed., vol. 1, 1004-1010.
Biegert et al., "Sequence Context-specific Profiles for Homology Searching," *PNAS* 2009, vol. 106, No. 10, 3770-3775.
Bjorn, "Clues emerge about benefits of briefly blocking blood flow," *Nature* Feb. 2009, vol. 15, No. 2, 132.
Blair et al., "Bathophenanthrolinedisulphonic Acid and Bathocuproinedisulphonic Acid, Water Soluble Reagents for Iron and Copper," *Talanta* 1961, vol. 7, Nos. 3-4, 163-174 (abstract).
Blakemore, "The modified Julia olefination: alkene synthesis via the condensation of metallated heteroarylalkylsulfones with carbonyl compounds," *J. Chem. Soc.* Perkin Trans. I, Nov. 4, 2002, 2563-2585.
Blanco et al., "6-Methylnitroarachidonate: A novel esterified nitroalkene that potently inhibits platelet aggregation and exerts cGMP-mediated vascular relaxation," *Free Radic. Biol. Med.* 2011, vol. 50, 411-418.
Bligh et al., "A Rapid Method of Total Lipid Extraction and Purification," *Can. J. Biochem. Physiol.* 1959, vol. 37, No. 8, 911-917.
Bloodsworth et al., "Nitric Oxide Regulation of Free Radical- and Enzyme-Medicated Lipid and Lipoprotein Oxidation," *Arterioscler. Thromb. Vasc. Biol.* Jul. 2000, vol. 20, 1707-1715.
Boden et al., "Free fatty acids in obesity and type 2 diabetes: defining their role in the development of insulin resistance and β-cell dysfunction," *Euro. J. Clin. Invest.* 2002, 32 (Suppl. 3), 14-23.
Bonacci et al., "Gas-Phase Fragmentation Analysis of Nitro-Fatty Acids," *J. Am. Soc. Mass Spec.* 2011, vol. 22, 1534-1551.
Bonacci et al., "Nitro-oleic Acid Improves Insulin Signaling via Protein Tyrosine Phosphatase-1b Inhibition," *Free Radical Bio. Med.* Jan. 1, 2008, Elsevier Science, vol. 45, Suppl. 1, S154 (abstract).
Bonacci et al., "Electrophilic Fatty Acids Regulate Matrix Metalloproteinase Activity and Expression," *J. Biolo. Chem.* 2011, vol. 286, No. 18, 16074-16081 (abstract).
Bonomi et al., "Direct Metal Ion Substitution at the $[M(Scys)_4]^2$ Site of Rubredoxin," *J. Biol. Inorg. Chem.* 1998, vol. 3, No. 6, 595-605.
Borniquel et al., "Nitrated oleic acid up-regulates PPARγ and attenuates experimental inflammatory bowel disease," *Free Radic. Bio. Med.* 2010, vol. 49, Iss. 4, 499-505.
Boruwa et al., "Catalytic Asymmetric Henry Reaction," *Tetrahedron: Asymmetry* Dec. 27, 2006, Report No. 90, 17, 3315-3326.
Burdge, "α-Linolenic Acid Metabolism in Men and Women: Nutritional and Biological Implications," *Clin. Nutri. Metabol. Care* 2004, vol. 7, 137-144.
Canadian Office Action issued on Apr. 24, 2015, by the Canadian Patent Office in corresponding Canadian Patent Application No. 2,729,053.
Castro et al., "Cytochrome c: a catalyst and target of nitrate-hydrogen peroxide-dependent protein nitration,"*Arch. Biochem. Biophys.* 2004, vol. 421, 99-107.
Chawla et al., "PPAR-γ dependent and independent effects on macrophage-gene expression in lipid metabolism and inflammation," *Nat. Med.* 2001, vol. 7, No. 1, 48-52.
Chen et al., "Peroxisome Proliferator-Activated Receptors and the Cardiovascular System," *Vitam. Horm.* 2003, vol. 66, 157-188.
Chen et al., "Synthesis and Screening of Novel Vitamin E Derivatives for Anticancer Functions," *European J. of Medicinal Chem.* 2012, vol. 58, 72-83.
Chen et al., "Troglitazone Inhibits Aterhosclerosis in Apolipoprotein E-Knockout Mice: Pleiotropic Effects on CD36 Expression and HDL," *Arterioscler. Thromb. Vasc. Biol.* 2001, vol. 21, 372-377.
Chinese First Office Action issued on Feb. 25, 2013, in Chinese Application No. 200980125943.4.
Clapp et al., "Oxygenation of Monounsaturated Fatty Acids by Soybean Liposygenase-1: Evidence for Transient Hydroperoxide Formation," *Biochem.* 2006, vol. 45, 15884-15892.
Claudel et al., "Reduction of atherosclerosis in apolipoprotein E knockout mice by activation of the retinoid X receptor," *Proc. Natl. Acad. Sci.* 2001, vol. 98, No. 5, 2610-2615.
Coffey et al., "Catalytic consumption of nitric oxide by 12/15-lipoxygenase. Inhibition of monocyte soluble guanylate cyclase activation," *Proc. Natl. Acad. Sci.* Jul. 3, 2001, vol. 98, No. 14, 8006-8011.
Cole et al., "Deciphering the Biology of *Mycobacterium tuberculosis* from the Complete Genome Sequence," *Nature* 1998, vol. 393, 537-544.
Cole et al., "Nitro-Fatty Acid Inhibition of Neointima Formation After Endoluminal Vessel Injury," *Circ. Res.* Nov. 6, 2009, 1-8; Suppl. Materials 1-6.

(56) References Cited

OTHER PUBLICATIONS

Coles et al., "Nitrolinoleate Inhibits Platelet Activation by Attenuating Calcium Mobilization and Inducing Phosphorylation of Vasodilator-stimulated Phosphoprotein through Elevation of cAMP," *J. Biol. Chem.* Feb. 22, 2002, vol. 277, No. 8, 5832-5840.

Coles et al., "Nitrolinoleate Inhibits Superoxide Generation, Degranulation, and Integrin Expression by Human Neutrophils. Novel Antiinflammatory Properties of Nitric Oxide-Derived Reactive Species in Vascular Cells," *Circ. Res.* Sep. 6, 2002, vol. 91, 375-381.

Collins et al., "Troglitazone Inhibits Formation of Early Atherosclerotic Lesions in Diabetic and Nondiabetic Low Density Lipoprotein Receptor-Deficient Mice," *Arterioscler. Thromb. Vasc. Biol.* 2001, vol. 21, 365-371.

Communication pursuant to Article 94(3) EPC for European Application No. 08 780 348.2 dated Jul. 26, 2011.

Cosby et al., "Nitrite reduction to nitric oxide by deoxyhemoglobin vasodilates the human circulation," *Nat. Med.* 2003, vol. 9, No. 12, 1498-1505.

Cowley et al., "The *Mycobacterium tuberculosis* Protein Serine/threonine Kinase PknG is Linked to Cellular Glutamate/glutamine Levels and is Important for Growth In Vivo," *Molecular Microbio.* 2004, vol. 52, No. 6, 1691-1702.

Dang et al. (Hung), "Anti-inflammatory Constituents of the Red Alga *Gracilaria verrucosa* and Their Synthetic Analogues," *J. Nat. Prod.* 2008, vol. 71, No. 2, 232-240.

Dangi et al., "Biogenic Synthesis, Purification, and Chemical Characterization of Anti-Inflammatory Resolvins Derived from Docosapentaenoic Acid (DPAn-6)," *J. Biol. Chem.* May 29, 2009, vol. 284, No. 22, 14744-14759.

Davies et al., "Oxidized Alkyl Phospholipids Are Specific, High Affinity Peroxisome Proliferator-activated Receptor γ Ligands and Agonists," *J. Biol. Chem.* May 11, 2001, vol. 276, No. 19, 16015-16023.

Defronzo et al., "Insulin Resistance: A Multifaceted Syndrome Responsible for NIDDM, Obesity, Hypertension, Dyslipidemia, and Atherosclerotic Cardiovascular Disease," *Diabetes Care* Mar. 1991, vol. 14, No. 3, 175-194.

Delerive et al., "Oxidized Phospholipids Activated PPARα in a Phospholipase A2-Dependent Manner," *FEBS Lett.* 2000, vol. 471, 34-38.

Del Mar Grassa et al., "Daily Oral Oleoyl-estrone Gavage Induces a Dose-dependent Loss of Fat in Wistar Rats," *Obesity Res.* Mar. 1, 2001, vol. 9, No. 3, 202-209.

De Meijere et al., "Metal-Catalyzed Cross-Coupling Reactions," *Wiley-VCH Verlag GMbH & Co.* 2004, Weinheim, vols. 1 and 2, XXII, ISBN-10: 3-527-30518-1 and ISBN-13: 978-3-527-30518-6 (TOC).

Denicola et al., "Diffusion of Nitric Oxide into Low Density Lipoprotein,"*J. Biol. Chem.* 2002, vol. 277, No. 2, 932-936.

Denicola et al., "Diffusion of peroxynitrite across erythrocyte membranes," *Proc. Natl. Acad. Sci.* 1998, vol. 95, 3566-3571.

Desper et al., "Getting a Tree Fast: Neighbor Joining, FastME, and Distance-Based Methods," *Curr. Protoc. Bioinformatics* 2006, Chap. 6, Unit 6.3.

d'Ischia, "Oxygen-Dependent Nitration of Ethyl Linoleate with Nitric Oxide," *Tetrahedron Lett.* 1996, vol. 37, No. 32, 5773-5774.

d'Ischia et al., "Medium-dependent Competitive Pathways in the Reactions of Polyunsaturated Fatty Acids with Nitric Oxide in the Presence of Oxygen. Structural Characterisation of Nitration Products and a Theoretical Insight," *Tetrahedron* 1999, vol. 55, 9297-9308.

Dodge et al., "Composition of phospholipids and of phospholipids fatty acids and aldehydes in human red cells," *J. Lipid Res.* 1967, vol. 8, 667-675.

Dorwald, "Side reactions in Organic Synthesis," 2005, Wiley-VCH, 1-16.

Easton et al., "Polyunsaturated Nitroalkanes and Nitro-Substituted Fatty Acides," *Synthesis* 2001, vol. 3, 451-457.

Eberhardt et al., "Prevalence of Overweight and Obesity Among Adults with Diagnosed Diabetes—United States, 1988-1994 and 1999-2002," *CDC*, Nov. 19, 2004; vol. 53, No. 45, 1066-1068.

Eiserich et al., "Myeloperoxidase, a Leukocyte-Derived Vascular NO Oxidase," *Sci.* Jun. 28, 2002, vol. 296, 2391-2394.

Eiserich et al., "Pathophysiology of Nitric Oxide and Related Species: Free Radical Reactions and Modification of Biomolecules," *Molec. Aspects Med.* 1998, vol. 19, 221-357.

European Office Action issued on Jul. 9, 2013, by the European Patent Office, in corresponding European Patent Application No. 09739186.6.

European Office Action issued on Dec. 19, 2014, by the European Patent Office, in corresponding European Patent Application No. 09739186.6.

Evans et al., "PPARs and the complex journey to obesity," *Nat. Med.* Apr. 2004, vol. 10, No. 4, 1-7.

Extended European Search Report and Written Opinion issued in corresponding foreign application, EP 10821313.3, 1-9 (Jul. 2013).

Extended European Search Report and Written Opinion issued in corresponding foreign application, EP 11804082.3, 1-5 (Nov. 29, 2013).

Extended European Search Report and Written Opinion issued in corresponding European Patent Application No. 12825790.4, 1-7 (Dec. 11, 2014).

Extended European Search Report and Written Opinion issued in corresponding European Patent Application No. 12839555.5, 1-6 (Feb. 2, 2015).

Extended European Search Report for EP08780348.2 (Jul. 30, 2010).

Extended European Search Report and Written Opinion issued in EP Patent Application No. 09732031.1 dated Dec. 22, 2011.

Extended European Search Report and Written Opinion issued in EP Patent Application No. 13743207.6-1464, dated Jun. 22, 2015.

Feelisch et al., "Concomitant S-, N-, and heme-nitros(yl)ation in biological tissues and fluids: implications for the fate of NO in vivo," *FASEB J.* Nov. 2002, vol. 16, 1775-1785.

Ferreira et al., "Macrophage activation induces formation of the anti-inflammatory lipid cholesteryl-nitrolinoleate," *Biochem. J.* 2009, vol. 417, 223-234.

Ferry et al., "Binding of prostaglandins to human PPARγ: tool assessment and new natural ligands," *Eur. J. Pharmacol.* 2001, vol. 417, 77-89.

Final Office Action dated Jul. 7, 2014, issued for U.S. Appl. No. 13/387,489.

Finlayson-Pitts et al., "A Fourier Transform Infrared Spectrometry Study of the Reactions of Phosphatidylcholines with Gaseous $N_2O_5$ and $NO_2$," *Toxicol. Appl. Pharmacol.* 1987, vol. 89, 438-448.

Fiuza et al., "From the Characterization of the Four Serine/Threonine Protein Kinases (PknA/B/G/L) of Corynebacterium Glutamicum Toward the Role of PknA and PknB in Cell Division," *J. Biolo. Chem.* 2008, vol. 283, No. 26, 10899-18112.

Forman et al., "15-Deoxy-$\Delta^{12,14}$—Prostaglandin $J_2$ is a Ligand for the Adipocyte Determination Factory PPARγ," *Cell* 1995, vol. 83, 803-812.

Freeman et al., "Nitro-fatty Acid Formation and Signaling," *J. of Biol. Chem.* Jun. 6, 2008, vol. 283, No. 23, 15515-15519.

Freshney, "Culture of Animal Cells," *A Manual of Basic Technique* 1983, Alan R. Liss, Inc., New York, 1-6.

Fu et al., "Oleylethanolamide regulates feeding and body weight through activation of the nuclear receptor PPAR-α," *Nature* Sep. 4, 2003, vol. 425, 90-93.

Furstner et al., "Total Synthesis of Epohelmin B and Its Analogues," *Chem. Asian J.* 2008, vol. 3, 310-318.

Gallon et al., "The Identification of the Allylic Nitrite and Nitro Derivatives of Methyl Linoleate and Methyl Linolenate by Negative Chemical Ionization Mass Spectroscopy," *Lipids* 1993, vol. 28, No. 2, 125-133.

Gallon et al., "The Reaction of Low Levels of Nitrogen Dioxide with Methyl Linoleate in the Presence and Absence of Oxygen," *Lipids* 1994, vol. 29, No. 3, 171-176.

(56) References Cited

OTHER PUBLICATIONS

Gavin III et al., "Reducing Cardiovascular Disease Risk in Patients with Type 2 Diabetes: A Message from the National Diabetes Education Program," *Am. Fam. Physician* Oct. 15, 2003, vol. 68, No. 8, 1569-74.
Gladwin et al., "The emerging biology of the nitrite anion," *Nature* Nov. 2005, vol. 1, No. 6, 308-314.
Gladwin et al., "Role of circulating nitrite and S-nitrosohemoglobin in the regulation of regional blood flow in humans," *Proc. Natl. Acad. Sci.* 2000, vol. 97, No. 21, 11482-11487.
Gladwin et al., "S-Nitrosohemoglobin is Unstable in the Reductive Erythrocyte Environment and Lacks $O_2$/NO-linked Allosteric Function," *J. Biol. Chem.* 2002, vol. 277, No. 31, 27818-27828.
Goodman & Gilman's *The Pharmacological Basis of Therapeutics*, Sixth Edition 1980, MacMillan Publishing Co., New York (TOC).
Goodman & Gilman's *The Pharmacological Basis of Therapeutics*, Ninth Edition 1996, McGraw-Hill Book Company, New York, Appendix II, 1707-1711 (TOC).
Goodman & Gilman's *The Pharmacological Basis of Therapeutics*, Tenth Edition 2001, McGraw-Hill Book Company, New York (TOC).
Gorczynski et al., "Evaluation of Nitroalkenes as Nitric Oxide Donors," *Bioorg. Med. Chem. Lett.* 2007, vol. 17, 2013-2017.
Gorczynski et al., "Regio-and Stereospecific Synthesis and Nitric Oxide Donor Properties of (E)-9- and (E)-10-Nitrooctadec-9-enoic Acids," *Org. Lett.* Apr. 25, 2006, vol. 8, No. 11, 2305-2308.
Grisham, "Myoglobin-Catalyzed Hydrogen Peroxide Dependent Arachidonic Acid Peroxidation," *Free Radic. Biol. Med.* 1985, vol. 1, 227-232.
Groeger et al., "Discovery, Structural Characterization and Quantification of Novel Inflammatory-Induced Electrophilic Fatty Acid Derivatives," *Free Radical Biology & Medicine* 2008, vol. 45, No. 1, S134.
Groeger et al., "Cyclooxygenase-2 generates anti-inflammatory mediators from omega-3 fatty acids," *Nat. Chem. Bio.* Jun. 2010, vol. 6, 433-441.
Groeger et al., "Signaling Actions of Electrophiles: Anti-inflammatory Therapeutic Candidates," *Molec. Interven.* Feb. 2010, vol. 10, Issue 1, 39-50.
Guindon et al., "A Simple, Fast, and Accurate Algorithm to Estimate Large Phylogenies by Maximum Likelihood," *Systematic Bio.* 2003, vol. 52, No. 5, 696-704.
Guindon et al., "Estimating Maximum Likelihood Phylogenies with PhyML," *Methods in Molecular Bio.* 2009, vol. 537, 113-137.
Guo et al., "Atypical PKCζ transduces electrophilic fatty acid signaling in pulmonary epithelial cells," *Nitric Oxide* 2011, vol. 25, 366-372.
Gutierrez et al., "Nitric Oxide Regulation of Superoxide-Dependent Lung Injury: Oxidant-Protective Actions of Endogenously Produced and Exogenously Administered Nitric Oxide," *Free Radic. Biol. Med.* 1996, vol. 21, No. 1, 43-52.
Hartmann et al., "A randomized trial comparing the nephrotoxicity of cisplatin/ifosfamide-based combination chemotherapy with or without amifostine in patients with solid tumors," *Investigational New Drugs* 2000, vol. 18, 281-289.
Hogg et al., "Reactions of Nitric Oxide With Nitronyl Nitroxides and Oxygen: Prediction of Nitrate Formation By Kinetic Simulation," *Free Radic. Res.* 1195, vol. 22, No. 1, 47-56.
Hogg et al, "Inhibition of low-density lipoprotein oxidation by nitric oxide Potential role in atherogenesis," *FEBS Lett.* 1993, vol. 334, No. 2, 170-174.
Hogg, "The Biochemistry and Physiology of S-nitrosothiols," *Annu. Rev. Pharmacol. Toxicol.* 2002, 42, 585-600.
Ichikawa et al., "Nitroalkenes Suppress Lipopolysaccharide-Induced Signal Transducer and Activator of Transcription Signaling in Macrophages: A Critical Role of Mitogen-Activated Protein Kinase Phosphatase 1," *Endocrinology* May 8, 2008, vol. 149, No. 8, 4086-4094.

Ignarro et al., "Endothelium-Derived Relaxing Factor From Pulmonary Artery and Vein Possesses Pharmacologic and Chemical Properties Identical to Those of Nitric Oxide Radical," *Circ. Res.* 1987, vol. 61, 866-879.
Ignarro et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," *J. Pharmacol. ExTher.* 1988, vol. 244, No. 1, 181-189.
Iles et al., "Fatty acid transduction of nitric oxide signaling: nitrolinoleic acid mediates protective effects through regulation of the ERK pathway," *Free Radic. Biol. Med.* 2009, vol. 46, 866-875.
International Preliminary Report on Patentability issued in corresponding PCT/US2012/051304, 1-8 (Mar. 6, 2014).
International Preliminary Report on Patentability issued in corresponding PCT/US2012/059722, 1-9 (Apr. 24, 2014).
International Search Report and Written Opinion mailed Dec. 4, 2009 corresponding to PCT/US2009/002628.
International Search Report and Written Opinion mailed Apr. 21, 2015 corresponding to PCT/US2014/065203.
International Search Report and Written Opinion mailed Aug. 19, 2013 corresponding to PCT/US2012/059722.
International Search Report and Written Opinion mailed Jul. 13, 2011 corresponding to PCT/US2010/051059.
International Search Report and Written Opinion mailed Jun. 2, 2013 corresponding to PCT/US2013/024476.
International Search Report and Written Opinion mailed Jun. 30, 2009 corresponding to PCT/US2009/041018.
International Search Report and Written Opinion mailed Mar. 23, 2012 corresponding to PCT/US2011/042011.
International Search Report and Written Opinion mailed Nov. 1, 2012 corresponding to PCT/US2012/051304.
International Search Report and Written Opinion mailed Oct. 12, 2006 corresponding to International Patent Application No. PCT/US2005/014305.
International Search Report and Written Opinion mailed Oct. 24, 2008 corresponding to International Patent Application No. PCT/US2008/009274.
International Search Report PCT/US2010/002141 dated Nov. 24, 2010.
Itoh et al., "Synthesis of Docosahexaenoic Acid Derivatives Designed as Novel PPARγ Agonists and Antidiabetic Agents," *Bioorg. Med. Chem.* 2006, vol. 14, 98-108.
Janero et al., "Differential nitros(yl)ation of blood and tissue constituents during glyceral trinitrate biotransformation in vivo," *PNAS* Nov. 30, 2004, vol. 101, No. 48, 16958-16963.
Japanese Office Action issued May 12, 2014, in Japanese Patent Application No. 2011-507440.
Japanese Office Action issued Oct. 15, 2013, in Japanese Patent Application No. 2011-507440.
Jeong et al., "Fenofibrate Prevents Obesity and Hypertriglyceridemia in Low-Density Lipoprotein Receptor-Null Mice," *Metabolism* May 2004, vol. 53, No. 5, 607-613.
Jimenez-Estrada et al., "Allyic Nitration of 3β-Sitosterol and Cholesterol Acetate: Preparation of 7-Nitro Derivatives," *Steroid* Jun. 1997, vol. 62, 500-503.
Jourd'Heuil et al., "The Oxidative and Nitrosative Chemistry of the Nitric Oxide/Superoxide Reaction in the Presence of Bicarbonate," *Arch. Biochem. Biophys.* 1999, vol. 365, No. 1, 92-100.
Kansanen et al., "Nrf2-Dependent and-Independent Responses to Nitro-fatty Acids in Human Endothelial Cells: Identification of Heat Shock Response as the Major Pathway Activated by Nitro-oleic Acid," *J. Biol. Chem.* Oct. 5, 2009, 1-34.
Karp et al., "Clinical and Biologic Activity of the Farnesyltransferase Inhibitor R115777 in Adults with Refractory and Relapsed Acute Leukemias: A Phase 1 Clinical-Laboratory Correlative Trial," *Blood* Jun. 2001, vol. 97, No. 11, 3361-3369.
Katoh et al., "Recent Developments in the MAFFT Multiple Sequence Alignment Program," *Briefings in Bioinformatics* 2008, vol. 9, No. 4, 286-298.
Kelley et al., "Nitro-oleic Acid, a Novel and Irreversible Inhibitor of Xanthine Oxidoreductase," *J. Biol. Chem.* Dec. 28, 2008, vol. 283, No. 52, 36176-36184.

(56) References Cited

OTHER PUBLICATIONS

Khoo et al., "Activation of vascular endothelial nitric oxide synthase and heme oxygenase-1 expression by electrophilic nitro-fatty acids," *Free Radic. Bio. Med.* 2010, vol. 48, 230-239.
Khoo et al., "Electrophilic nitro-fatty acids: anti-inflammatory mediators in the vascular compartment," *Curr. Opn. Pharml.* 2010, vol. 10, 179-184.
Kim et al., "Bisubstrate Ketone Analogues as Serotonin N-Acetyltransferase Inhibitors," *J. Med. Chem.* 2001, vol. 44, No. 15, 2479-2485.
Kissner et al., "Formation and Properties of Peroxynitrite as Studied by Laser Flash Photolysis, High-Pressure Stopped-Flow Technique, and Pulse Radiolysis," *Chem. Res. Toxicol.* Sep. 4, 1997, vol. 10, 1285-1292.
Kliewer et al. "A Prostaglandin $J_2$ Metabolite Binds Peroxisome Proliferatory-Activated Receptor γ and Promotes Adipocyte Differentiation," *Cell* 1995, vol. 83, 813-819.
Kliewer et al., "Fatty acids and eicosanoids regulate gene expression through direct interactions and peroxisome proliferator-activated receptors α and γ," *Proc. Natl. Acad. Sci.* Apr. 1997, vol. 94, 4318-4323.
Kobayshi, "The Reaction of Nitrogen Dioxide with Lung Surface Components: The Reaction with cis-9-octadecenoic Acid," *Chemosphere* 1983, vol. 12, No. 9/10, 1317-1325.
Koenitzer et al., "Redox signaling in inflammation: interactions of endogenous electrophiles and mitochondria in cardiovascular disease," *Ann. N.Y. Acad. Sci.* 2010, vol. 1203, 45-52.
Lai et al., "Reactions of Dinitrogen Pentoxide and Nitrogen Dioxide with 1-Palmitoyl-2-Oleoyl-sn-Glycero-3-Phosphocholine," *Lipids* 1991, vol. 26(4), 306-314. Abstract.
Lärfars et al., "Activation of Nitric Oxide Release and Oxidative Metabolism by Leukotrienes B4, C4, and D4 in Human Polymorphonuclear Leukocytes," *Blood* Feb. 15, 1999, vol. 93, No. 4, 1399-1405.
Lee et al., "Peroxisome proliferators-activated receptor-γ in macrophage lipid homeostasis," *Trends Endocrinol. Metab.* Oct. 2002, vol. 13, No. 8, 331-335.
Lee et al., "Rosiglitazone ameliorates cisplatin-induced renal injury in mice," *Nephrol. Dial. Transplant.* May 23, 2006, vol. 21, 2096-2105.
Levy et al., "Lipid mediator class switching during acute inflammation: signals in resolution," *Nat. Immunol.* Jul. 2001, vol. 2, No. 7, 612-619.
Li et al., "Molecular recognition of nitrated fatty acids by PPARγ," *Nat. Struct. Mol. Biol.* 2008, 1-3.
Li et al., "Differential inhibition of macrophage foam-cell formation and atherosclerosis in mice by PPARalpha, betta/delta, and gamma," *J. Clin. Invest.* 2004, vol. 114, No. 11, 1564-1576.
Lima et al., "Characterization of Linoleic Acid Nitration in Human Blood Plasma by Mass Spectrometry," *Biochem.* 2002, vol. 41, No. 34, 10717-10722.
Lima et al., "Cholesteryl Nitrolinoleate, a Nitrated Lipid Present in Human Blood Plasma and Lipoproteins," *J. Lipid Res.* 2003, vol. 44, 1660-1666.
Lima et al., "Nitrated Lipids Decompose to Nitric Oxide and Lipid Radicals and Cause Vasorelaxation," *Free Radical Bio. Med.* 2005, Elsevier Sciences, vol. 39, No. 4, 532-539.
Liu et al., "Accelerated reaction of nitric oxide with $O_2$ within the hydrophobic interior of biological membranes," *Proc. Natl. Acad. Sci.* Mar. 1998, vol. 95, 2175-2179.
Liu et al., "Combined losartan and nitro-oleic acid remarkably improves diabetic nephrophaty in mice," *Am. J. Physiol. Renal Physiol.* Aug. 14, 2013, vol. 305, F1555-F1562.
Lopez et al., "Second Generation of α-Tocopherol Analogs-Nitric Oxide Donors: Synthesis, Physiochemical, and Biological Characterization," *Bioorg. Med. Chem.* 2007, vol. 15, 6262-6272.
Löytynoja et al., "An Algorithm for Progressive Multiple Alignment of Sequences with Insertions," *PNAS* Jul. 26, 2005, vol. 102, No. 30, 10557-10562.

Lundberg et al., "Nitrate and nitrite in biology, nutrition and therapeutics," *Nat. Chem. Bio.* Dec. 2009, vol. 5, No. 12, 865-869.
Luzzio, "The Henry reaction: recent examples," *Tetrahedron* 2001, vol. 57, 915-945.
Ma et al., "Hydrohalogenation Reaction of Substituted 1, 2-Allenic Carboxylic Acids, Esters, Amides, Nitriles, and Diphenyl Phosphine Oxides," *Synthesis* Dec. 4, 2001, No. 5, 713-730.
March, "Effects of Structure on Reactivity," *Advanced Organic Chemistry* (1977 edition), McGraw-Hill Book Company, New York, 251-259.
Marnett et al., "Regulation of Prostaglandin Biosynthesis by Nitric Oxide is Revealed by Targeted Deletion of Inducible Nitric-oxide Synthese," *J. Biol. Chem.* 2000, vol. 275, No. 18, 13427-13430.
Marshall et al., "Nitrosation and oxidation in the regulation of gene expression," *FASEB J.* 2000, vol. 14, 1889-1900.
Marx et al., "Peroxisome Proliferator-Activated Receptors and Atherogenesis: Regulators of Gene Expression in Vascular Cells," *Circ. Res.* May 14, 2004, vol. 94, No. 9, 1168-1178.
McIntyre et al., "Identification of an intracellular receptor for lysophosphatidic acid (LPA): LPA is a transcellular PPARγ agonist," *Proc. Natl. Acad. Sci.* 2003, vol. 100(1), 131-136.
Menendez et al., "Effects of gama-linolenic acid and oleic acid on paclitaxel cytotoxicity in human breast cancer cells," *European J. of Cancer* (Oxford, England: 1990) Feb. 2001, vol. 37, No. 3, 402-213.
Messerschmidt et al., *Handbook of Metalloproteins* 2001, Hoboken, NJ, John Wiley & Sons, Inc. (abstract).
Minghetti, "Cyclooxygenase-2 (COX-2) in Inflammatory and Degenerative Brain Diseases," *J. Neuropathol. Exp. Neurol.* Sep. 2004, vol. 63, No. 9, 901-910.
Miranda et al., "The Chemical Biology of Nitric Oxide," *Nitric Oxide: Biology and Pathobiology* 2000, Academic Press, San Diego, 41-55.
Mitschke et al., "9- and 10-Nitro-oleic Acid Do Not Interfere with the GC-MS Quantitative Determination of Nitrite and Nitrate in Biological Fluids When Measured as Their Pentalfluorobenzyl Derivatives," *J. Chromatography B.* 2007, vol. 85, Issue 1, 287-291.
Montuschi et al., "Isoprostanes: markers and mediators of oxidative stress," *FASEB J.* Dec. 2004, vol. 18, 1791-1800.
Morgan et al., "Use of Animal Models of Human Disease for Nonclinical Safety Assessment of Novel Pharmaceuticals," *Toxicol. Pathol.* 2013, vol. 41, No. 3, 508-518.
Mukherjee et al., "A Selective Peroxisome Proliferator-Activated Receptor-γ (PPARγ) Modulatory Blocks Adipocyte Differentiation byt Stimulates Glucose uptake in 3T3-L1 Adipocytes," *Mol. Endocrinol.* 2000, vol. 14, 1425-1433.
Nadtochiy et al. "Mitochondrial nitroalkene formation and mild uncoupling in ischaemic preconditioning: implications for cardioprotection," *Card. Res. Adv. Access* 2008, 1-8.
Nadtochiy et al., "Nitroalkenes Confer Acute Cardioprotection via Adenine Nucleotide Transloase 1," *J. Biol. Chem.* Jan. 27, 2012, vol. 287, No. 5, 3573-3580.
Nagy et al., "Oxidized LDL Regulates Macrophage Gene Expression through Ligand Activation of PPARγ," *Cell* 1998, vol. 93, 229-240.
Napolitano et al., "Acid-Promoted Reactions of Ethyl Linoleate with Nitrite Ions: Formation and Structural Characterization of Isomeric Nitroalkene, Nitrohydroxy, and Novel 3-Nitro-1,5-hexadiene and 1,5-Dinitro-1,3-pentadiene Products," *J. Org. Chem.* 2000, vol. 65, No. 16, 4853-4860.
Napolitano et al., "The acid-promoted reaction of ethyl linoleate with nitrite. New insights from $^{15}$N-labelling and peculiar reactivity of a model skipped diene," *Tetrahedron* 2002, vol. 58, 5061-5067.
Napolitano et al., "Acid-Induced Structural Modifications of Unsaturated Fatty Acids and Phenolic Olive Oil Constituents by Nitrite Ions: A Chemical Assessment," *Chem. Res. Toxicol.* 2004, vol. 17, 1329-1337.
Narayan et al., "Serine Threonine Protein Kinases of *Mycobacterial* Genus: Phylogeny to Function," *Physiological Genomics* 2007, vol. 29, 66-75.
Nathan, "Nitric oxide as a secretory product of mammalian cells," *FASEB J.* 1992, vol. 6, 3051-3064.

(56) References Cited

OTHER PUBLICATIONS

Newman et al., "Optimized Thiol Derivatizing Reagent for the Mass Spectral Analysis of Distributed Epoxy Fatty Acids," *J. Chromato.* May 22, 2011, No. 925, 223-240.
Niebisch et al., "Corynebacterial Protein Kinase G Controls 2-Oxoglutarate Dehydrogenase Activity via the Phosphorylation Status of the Odhl Protein," *J. Biolo. Chem.* 2006, vol. 281, No. 18, 12300-12307.
Notredame et al., "T-Coffee: A novel method for fast and accurate multiple sequence alignment," *J. Molec. Bio.* 2000, vol. 302, 205-217.
Nott et al., "An Intramolecular Switch Regulates Phosphoindependent FHA Domain Interactions in *Mycobacterium tuberculosis*," *Sci. Signaling* 2009, vol. 2, No. 63, ra 12.
O'Donnell et al., "Interactions Between Nitric Oxide and Lipid Oxidation Pathways: Implications for Vascular Disease," *Circ. Res.* 2001, vol. 88, 12-21.
O'Donnell et al., "15-Lipoxygenase Catalytically Consumes Nitric Oxide and Impairs Activation of Guanylae Cyclase," *J. Biol. Chem.* Jul. 16, 1999, vol. 274, No. 29, 20083-20091.
O'Donnell et al., "Catalytic Consumption of Nitric Oxide by Prostagladin H Synthase-1 Regulates Platelet Function," *J. Biol. Chem.* Dec. 8, 2000, vol. 275, No. 49, 38239-38244.
O'Donnell et al., "Nitration of Unsaturated Fatty Acids by Nitric Oxide-Derived Reactive Nitrogen Species Peroxynitrite, Nitrous Acid, Nitrogen Dioxide, and Nitronium Ion," *Chem. Res. Toxicol.* 1999, vol. 12, No. 1, 83-92.
O'Donnell et al., "Nitric Oxide Inhibition of Lipid Peroxidation: Kinetics of Reaction with Lipid Peroxyl Radicals and Comparison with α-Tocopherol," *Biochem.* 1997, vol. 36, No. 49, 15216-15223.
Office Action issued on Nov. 21, 2013, for U.S. Appl. No. 13/387,489.
Office Action issued on Aug. 27, 2010, by the Japanese Patent Office in corresponding Japanese Patent Application No. 2014-186472, and a partial English Translation of the Office Action.
Office Action issued on Mar. 16, 2012, for corresponding foreign application, Chinese Patent Application No. 200980123324.1 (English translation).
Office Action issued on May 5, 2014, for corresponding foreign application CN201310054350.1 (English translation).
O'Hare et al., "Regulation of Glutamate Metabolism by Protein Kinases in Mycobacteria," *Mol. Microbio.* 2008, vol. 70, No. 6, 1408-1423.
Ono et al., "A Convenient Procedure for the Conversion of (E)-Nitroalkenes to (Z)-Nitroalkenes via erythro-β-Nitroselenides," *J. Chem. Soc., Chem Commun.* 1987, 1550-1551.
Ortiz-Lombardia et al., "Crystal Structure of the Catalytic Domain of the PknB Serine/Threonine Kinase from *Mycobacterium tuberculosis*," *J. Biolo. Chem.* 2003, vol. 278, No. 15, 13094-13100.
Padmaja et al., "The Reaction of Nitric Oxide With Organic Peroxyl Radicals," *Biochem. Biophys. Res. Commun.* 1993, vol. 195, No. 2, 539-544.
Park et al., "Modulation of Tumor Necrosis Factor-Related Apoptosis-Inducing Ligand-Induced Apoptosis by Chemotherapy in Thyroid Cancer Cell Lines," *Thyroid* 2003, vol. 13. No. 12, 1103-1110.
Pawliczak et al., "85-kDa Cytosolic Phospholipase $A_2$ Mediates Peroxisome Proliferatoractivated Receptor γ Activation in Human Lung Epithelial Cells,"*J. Biol. Chem.* 2002, vol. 277, 33153-33163.
Pryor et al., "Reaction of Nitrogen Dioxide with Alkenes and Polyunsaturated Fatty Acids: Addition and Hydrogen Abstraction Mechanisms," *J. Amer. Chem. Soc.* 1982, vol. 104, 6685-6692.
Punchard et al., The Journal of Inflammation Editorial, Sep. 27, 2004, *The Journal of Inflammation*, BioMed Central, vol. 1, No. 1, 1-4.
Quijano et al., "Reaction of Peroxynitrite with Mn-Superoxide Dismutase: Role of the Metal Center in Decomposition Kinetics and Nitration," *J. of Biol. Chem.* Apr. 13, 2001, vol. 276, No. 15, 11631-11638.
Radi et al., "Peroxynitrite Oxidation of Sulfhydryls: The Cytotoxic Potential of Superoxide and Nitric Oxide," *J. Biol. Chem.* 1991, vol. 266, No. 7, 4244-4250.
Radi et al., "Peroxynitrite Reactions with Carbon Dioxide-Bicarbonate," *Methods Enzymol.* 1999, vol. 301, No. 37, 353-367.
Ranu et al., "Highly Selective Reduction of Conjugated Nitroalkenes with Zinc Borohydride in DME," *Tetrahedron Letters* 1991, vol. 32, No. 29, 3579-3582.
Rassaf et al., "Concomitant Presence of N-Nitroso and S-Nitroso Proteins in Human Plasma," *Free Radic. Biol. Med.* 2002, vol. 33, No. 11, 1590-1596.
Rassaf et al., "NO adducts in mammalian red blood cells: too much or too little?" *Nat. Med.* 2003, vol. 9, No. 5, 481-482.
Remington's *Pharmaceutical Sciences* 1990, 18th Ed. (TOC).
Rosen et al., "PPARγ: a Nuclear Regulator of Metabolism, Differentiation, and Cell Growth," *J. Biol. Chem.* 2001, vol. 276, No. 1, 37731-37734.
Rowe et al., "Acesulfame Potassium," *Handbook of Pharma. Excipients* 2006, 5th Ed., Great Britain: Pharmaceutical Press (abstract).
Rowe et al., *Handbook of Pharma. Excipients* 2006, 5th Ed., Great Britain: Pharmaceutical Press, American Pharmacists Association.
Rubbo et al., "Form on Nitric Oxide: Chemical Events in Toxicity. Nitrix Oxide Regulation of Tissue Free Radical Injury," *Chem. Res. Toxicol.* 1996, vol. 9, No. 5, 809-820.
Rubbo et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives," *Arch. Biochem. Biophys.* Dec. 1, 1995, vol. 324, No. 1, 15-25.
Rubbo et al., "Nitric Oxide Reaction with Lipid Peroxyl Radicals Spares α-Tocopherol during Lipid Peroxidation," *J. Biol. Chem.* 2000, vol. 275, No. 25, 10812-10818.
Rubbo et al., "Nitric Oxide Regulation of Superoxide and Peroxynitrite-dependent Lipid Peroxidation," *J. Biol. Chem.* Oct. 21, 1994, vol. 269, No. 42, 26066-26075.
Rudnick et al., "Contrast-induced nephropathy: How it develops, how to prevent it," *Cleveland Clinic J. Med.* Jan. 2006, vol. 73, No. 1, 75-87.
Rudolph et al., "Cardiovascular Consequences When Nitric Oxide and Lipid Signaling Converge," *Circ. Res.* Sep. 11, 2009, vol. 105, 511-522.
Rudolph et al., "Endogenous generation and protective effects of nitro-fatty acids in murine model of focal cardiac ischaemia and reperfusion," *Cardiov. Res. Advance Access* 2009, 1-12.
Rudolph et al., "Nitro-fatty Acid Metabolome: Saturation, Desaturation, β-Oxidation, and Protein Adduction," *J. Biol. Chem.* Jan. 16, 2009, vol. 284, No. 3, 1461-1473.
Rudolph et al., "Nitro-Fatty Acids Reduce Atherosclerosis in Apolipoprotein E-Deficient Mice," *Ather. Thromb. Vasc. Bio.* May 2010, vol. 30, 938-945.
Rudolph et al., "Transduction of Redox Signaling by Electrophile-Protein Reactions," *Sc. Signaling* Sep. 29, 2009, vol. 2, Issue 90 re7 1-13.
Ryan et al., "Diabetes and the Mediterranean Diet: a Beneficial Effect of Oleic Acid on Insulin Sensitivity, Adipocyte Glucose Transport and Endothelium-dependent Vasoreactivity," *Q. J Med.* 2000, vol. 93, 85-91.
Saffer et al., "Choosing Drug Therapy for Patients with Hyperlipidemia," *Am. Fam. Physic.* Jun. 1, 2000, vol. 61, No. 11, 3371-3382.
Sarver et al., "Analysis of Peptides and Proteins Containing Nitrotyrosine by Matrix-assisted Laser Desorption/ionization Mass Spectrometry, " *J. Am. Soc. Mass Spectrom.* 2001, vol. 12, No. 4, 439-448.
Satyanarayana et al., "Steroselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," *Organometallics* 1991, vol. 10, 804-807.
Saulnier-Blache et al., "A simple and highly sensitive radioenzymatic assay for lysophosphatidic acid quantification," *J. Lipid Res.* 2000, vol. 41, 1947-1951.

(56) References Cited

OTHER PUBLICATIONS

Scarpini et al., "Treatment of Alzheimer's Disease: Current Status and New Perspectives," *Lancet Neurol.* Sep. 2003, vol. 2, 539-547.
Scherr et al., "Structural Basis for the Specific Inhibition of Protein Kinase G, a Virulence Factor of *Mycobacterium tuberculosis*," *PNAS* 2007, vol. 104, No. 29, 12151-12156.
Schopfer et al., "Fatty Acid Transduction of Nitric Oxide Signaling. Nitrolinoleic Acid is a Hydrophobically Stabilized Nitric Oxide Donor," *J. Biol. Chem.* May 13, 2005, vol. 280, No. 19, 19289-19297.
Schopfer et al., "NO-dependent protein nitration: a cell signaling event or an oxidative inflammatory response?" *Trends Biochem. Sci.* 2003, vol. 28, 646-654.
Schopfer et al., "Covalent Peroxisome Proliferator-activated Receptor γ Adduction by Nitro-fatty Acids: Selective ligand activity and anti-diabetic signaling actions," *J. Biol. Chem.* Apr. 16, 2010, vol. 285, No. 16, 12321-12333.
Schopfer et al., "Detection and quantification of protein adduction by electrophilic fatty acids: mitochondrial generation of fatty acid nitroalkene derivatives," *Free Radic. Biol. Med.* 2009, vol. 46, 1250-1259.
Sculptoreanu et al., "Nitro-Oleic Acid Inhibits Firing and Activates TRPV-1 and TRPA1-Mediated Inward Currents in Dorsal Root Ganglion Neurons from Adult Male Rats," *J. Pharm. Expt. Thera.* 2010, vol. 333, No. 3, 883-895.
Serhan et al., "Anti-Inflammatory Actions of Neuroprotectin D1/Protectin D1 and Its Natural Stereoisomers: Assignments of Dihydroxy-Containing Docosatrienes," *J. Immunology* 2006, vol. 176, 1848-1859.
Setiadi et al., "Vitamin E models. Conformational analysis and stereochemistry of tetralin, choman, thiochroman and selenochroman," *J. Molecular Structure (Theochem)* 2002, vol. 594, 161-172.
Sharpless et al., "A Mild Procedure for the Conversion of Epoxides to Allylic Alcohols. The First Organoselenium Reagent," *J. Am. Chem. Soc.* Apr. 18, 1973, vol. 95, No. 8, 2697-2699.
Sieker et al., "Rubredoxin in Crystalline State," *Methods Enzymol.* 1994, vol. 243, 203-216.
Simopoulos et al., "Omega-3 Fatty Acids in Inflammation and Autoimmune Diseases," *J. Amer. College of Nutrition* 2002, vol. 21, No. 6, 495-505.
Smith, "Prostanoid biosynthesis and mechanisms of action," *Am. Physiol. Soc.* 1992, vol. 263, F181-F191.
Snider et al., "Oxidative and Dehydrative Cyclizations of Nitroacetate Esters with Mn(Oac)$_3$," *Tetrahedron*, Sep. 23, 2002, vol. 58, No. 39, 7821-7827.
Söding et al., "HHsenser: Exhaustive Transitive Profile Search Using HMM-HMM Comparison," *Nucleic Acids Res.* 2006, vol. 34, W374-378.
Strowig et al., "Combination therapy using metformin or thiazolidinediones and insulin in the treatment of diabetes mellitus," *Diabetes, Obesity, and Metabolism* 2005, vol. 7, 633-641.
Subczynski et al., "Permeability of Nitric Oxide through Lipid Bilayer Membranes," *Free Radic. Res.* 1996, vol. 24, 343-349.
Summons to Attend Oral Proceedings dated Oct. 2, 2012, from corresponding European Patent Application No. 08780348.2.
Szekely et al., "A Novel Drug Discovery Concept for Tuberculosis. Inhibition of Bacterial and Host Cell Signaling," *Immun. Letters* 2008, vol. 116, No. 2, 225-231.
Szoka et al., "Comparative Properties and Methods of Preparation of Lipid Vesicles (Liposomes)," *Annu. Rev. Biophys. Bioeng.* 1980, vol. 9, 467-508.
Tang et al., "Nitroalkenes induce rat aortic smooth muscle cell apoptosis via activation of caspase-dependent pathways," *Biochem. Biophys. Res. Commun.* 2010, vol. 397, 239-244.
Thatcher et al., "Nitrates and NO Release: Contemporary Aspects in Biological and Medicinal Chemistry," *Free Radic. Biol. Med.* 2004, vol. 37, No. 8, 1122-1143.
Thomas et al., "The biological lifetime of nitric oxide. Implications for the perivascular dynamics of NO and $O_2$," *Proc. Natl. Acad. Sci.* Jan. 2, 2001, vol. 98, No. 1, 355-360.

Tiwari et al., "Key Residues in *Mycobacterium tuberculosis* Protein Kinase G Play a Role in Regulating Kinase Activity and Survival in the Host," *J. Biolol. Chem.* 2009, vol. 284, No. 40, 27467-27479.
Tontonoz et al., "Stimulation of Adipogenesis in Fibroblasts by PPARγ2, a Lipid-Activated Transcription Factor," *Cell* 1994, vol. 79, 1147-1156.
Tontonoz et al., "mPPARγ2: tissue-specific regulator of an adipocyte enhancer," *Genes Dev.* 1994, vol. 8, No. 10, 1224-1234.
Toth, "High-Density Lipoprotein and Cardiovascular Risk," *Circulation* 2004, vol. 109, 1809-1812.
Trostchansky et al., "Nitrated Fatty Acids: Mechanisms of Formation, Chemical Characterization, and Biological Properties," *Free Rad. Biol. Med.* 2008, vol. 44, 1887-1896.
Tsikas et al., "Nitro-fatty Acids Occur in Human Plasma in the Picomolar Range: a Targeted Nitro-lipidomics GC-MS/MS Study," *Lipids* 2009, vol. 44, 855-865.
Tzameli et al., "Regulated Production of a Peroxisome Proliferatory-Activated Receptor-gamma Ligand during an Early Phase of Adipocyte Differentiation in 3T3-L1 Adipocytes," *J. Biol. Chem.* 2004, vol. 279, No. 34, 36093-36102.
U.S. Appl. No. 13/646,985, Non-Final Office Action mailed Jun. 12, 2014.
U.S. Appl. No. 13/646,985, Non-Final Office Action mailed May 1, 2014.
U.S. Appl. No. 13/646,985, Notice of Allowance, Dec. 5, 2014.
U.S. Appl. No. 14/638,370, Non-Final Office Action, Jul. 8, 2015.
U.S. Appl. No. 14/638,370, Notice of Allowance, Nov. 18, 2015.
Van Beilen et al., "Rubredoxins Involved in Alkane Oxidation," *J. Biolol. Chem.* 2002, vol. 184, No. 6, 1722-1732.
Vickers et al., "IGF-1 Treatment Reduces Hyperphagia, Obesity, and Hypertension in Metabolic Disorders Induced by Fetal Programming," *Endocrinol.* Sep. 2001, vol. 142, No. 9, 3964-3973.
Vidwans et al., "Differential Modulation of Prostaglandin H Synthase-2 by Nitric Oxide-Related Species in Intact Cells," *Biochem.* 2001, vol. 40, 11533-11542.
Villacorta et al., "Nitro-linoleic Acid Inhibits Vascular Smooth Muscle Cell Proliferation via the Keap1/Nrf2 Signaling Pathway," *Am. J. Physiol. Heart Circ. Physiol.* Apr. 27, 2007, 1-9.
Villacorta et al., "PPARγ and its ligands: therapeutic implications in cardiovascular disease," *Clin. Sci.* 2009, vol. 116, 205-218.
Villarino et al., "Proteomic Identification of M. Tuberculosis Protein Kinase Substrates: PknB Recruits GarA, a FHA Domain-containing Protein, Through Activation Loop-mediated Interactions," *J. Mol. Bio.* 2005, vol. 350, No. 5, 953-963.
Von Knethen et al., "Activation of Peroxisome Proliferator-Activated Receptor γ by Nitric Oxide in Monocytes/Macrophages Down-Regulates p47$^{phox}$ and Attenuates the Respiratory Burst," *J. Immunol.* 2002, vol. 169, 2619-2626.
Walburger et al., "Protein Kinase G from Pathogenic Mycobacteria Promotes Survival Within Macrophages," *Sci.* 2004, vol. 304, 1800-1804.
Wang et al., "Constitutive Activation of Peroxisome Proliferator-activated Receptor-γ Suppresses Pro-inflammatory Adhesion Molecules in Human Vascular Endothelial Cells," *J. Biol. Chem.* 2002, vol. 277, No. 37, 34176-34181.
Wang et al., "Effects of Endogenous PPAR Agonist Nitro-Oleic Acid on Metabolic Syndrome in Obese Zucker Rats," *PPAR Res.* 2010, vol. 2010, Art. ID 601562, 1-7.
Wang et al., "Nitro-oleic acid protects against endotoxin-induced endotoxemia and multiorgan injury in mice," *Am. J Physiol. Renal Physiol.* Dec. 23, 2009, vol. 298, F754-762.
Weber et al., "Fragmentation of Bovine Serum Albumin by Pepsin. 1. The Origin of the Acid Expansion of the Albumin Molecule," *J. Biolo. Chem.* 1964, vol. 239, No. 5, 1415-1423.
Wehenkel et al., "Mycobacterial Ser/Thr Protein Kinases and Phosphatases: Physiological Roles and Therapeutic Potential," *Biochemica et biophysica acta* 2008, vol. 1784, No. 1, 193-202.
Woodcock, "Synthesis of Nitrolipids. All Four Possible Diastereomers of Nitrooleic Acids: (E)- and (Z)-, 9- and 10-Nitro-octadec-9-enoic Acids," *Organic Letters* 2006, vol. 8, No. 18, 3931-3934.
Wright et al., "Fatty acid transduction of nitric oxide signaling: Nitrolinoleic acid potently activates endothelial heme oxygenase 1 expression," *PNAS* Mar. 14, 2006, vol. 103, No. 11, 4299-4304.

(56) References Cited

OTHER PUBLICATIONS

Wright et al., "Human Heme Oxygenase-1 Induction by Nitrolinoleic Acid is Mediated by cyclic AMP, AP-1, and E-box Response Element Interactions," *Biochem. J.* 2009, m. BJ20090339, 1-31.
Written Opinion issued in corresponding PCT/US2012/059722, 1-8 (Aug. 19, 2013).
Xu et al., "Lysophosphatidic Acid as a Potential Biomaker for Ovarian and Other Gynecologic Cancers," *JAMA* 1998, vol. 280, 719-723.
Zhang et al., "Lysophosphatidic Acid Induces Neointima Formation Through PPARgamma Activation," *J. ExMed.* 2004, vol. 199, No. 6, 763-774.
Zhang et al., "Selective disruption of PPARgamma2 impairs the development of adipose tissue and insulin sensitivity," *Proc. Natl. Acad. Sci.* 2004, vol. 101, No. 29, 10703-10708.
Zhang et al., "Nitro-Oleic Acid Inhibits Angiotensin II-Induced Hypertension," *Circ. Res.* 2010, vol. 107, 540-548.
Dembitsky et al., "Natural halogenated fatty acids: their analogues and derivatives," *Progress in Lipid Research* 2002, vol. 41, No. 4, 315-367.
Duan et al., "Nephrotoxicity of high- and low-osmolar contrast media: Protective role of forsinopril or telmisartan in a rat model," *J. Central S. Univ.* (Dec. 31, 2007), vol. 32, No. 5, 812-818.
Extended European Search Report and Written Opinion issued in corresponding European Patent Application No. 16157509.7, 1-9 (May 30, 2016).
Manini et al., "Chemistry of Nitrated lipids: Remarkable Instability of 9-Nitrolinoleic Acid in Neutral Aqueous Medium and a Novel Nitronitrate Ester Product by Concurrent Autoxidation/Nitric Oxide-Release Pathways," *J. Org. Chem.* 2008, vol. 73, No. 19, 7517-7525.
Office Action issued in corresponding foreign application CN201310054350.1 (Jan. 13, 2015).
Office Action (Second) issued in corresponding foreign application CN201280057123.8 (May 17, 2016) (English Translation).

* cited by examiner

USE OF NITRATED LIPIDS FOR TREATMENT OF SIDE EFFECTS OF TOXIC MEDICAL THERAPIES

CROSS-REFERENCE TO RELATED APPLICATIONS

The present application is a continuation of U.S. Ser. No. 12/996,848 filed Mar. 4, 2011, which claims the benefit of International Application No. PCT/US2009/047825, International Filing Date Jun. 18, 2009, which claims the benefit of U.S. Provisional Application No. 61/073,945 filed on Jun. 19, 2008, all of which are incorporated herein by reference in their entireties.

STATEMENT OF GOVERNMENT RIGHTS

This invention was made with government support under RO-1 HL079453 and RO-1 DK 066592 by the National Institutes of Health. The government has certain rights to this invention.

FIELD OF THE INVENTION

The present invention relates to methods of treating the side effects of a toxic medical therapy using nitrated lipids. In particular, the methods comprise the use of nitrated fatty acids or esters thereof to treat side effects, including organ system damage, caused by chemotherapy, radiotherapy, and the administration of other toxic agents.

BACKGROUND OF THE INVENTION

Chemotherapy and radiotherapy provide an effective means of treating cancer. For example, cisplatin is among of the most successful anticancer drugs and is now being widely used for the treatment of testicular, head and neck, ovarian, cervical, nonsmall cell lung carcinoma, and many other types of cancer. In addition, approximately half of cancer patients received radiotherapy as a single and adjuvant therapy at some stage of their illness. However, a drawback of both chemotherapy and radiotherapy is the production of toxicity in normal tissues. For example, the clinical use of cisplatin is limited by its severe side effects, including neurotoxicity, ototoxicity, nausea and vomiting, hair loss, and nephrotoxicity. The mechanism of cisplatin-induced organ damage has been shown to be multifactorial, involving oxidative stress and apoptosis. Other kinds of medical treatment may also involve administration of toxic agents, i.e., those that produce toxicity in normal tissues. Like chemotherapy and radiotherapy, the side effects associated with such treatments may limit the use of the treatment.

SUMMARY

In one aspect, the present invention provides methods and medicaments useful in the treatment of the side effects of toxic medical therapies. The methods involve administration of at least one nitrated lipid to a subject in need thereof in amounts effective to treat a side effect of a toxic medical therapy. In some embodiments of the present methods, the side effect is reduced relative to the side effect prior to administration of the nitrated fatty acid or ester thereof. The nitrated lipids may be used to prepare medicaments for treating a side effect of a toxic medical therapy.

A variety of nitrated lipids may be used in the present methods, including, e.g., nitrated fatty acids and esters thereof. In some embodiments, the nitrated fatty acid is a monounsaturated fatty acid (e.g., oleic acid) or a polyunsaturated fatty acid. In illustrative embodiments, the oleic acid is selected from 9-nitrooleic acid, 10-nitrooleic acid, or combinations thereof.

Form the methods disclosed herein, a variety of lipids may be used to form the nitrated lipids, including, but not limited to a fatty acid or an ester thereof. Similarly, a variety of fatty acids are compatible with the disclosed methods, including, but not limited to, monounsaturated and polyunsaturated fatty acids.

Procedures for synthesizing nitrated lipids, sources for obtaining the lipids, and administration routes for the nitrated lipids are also provided.

Using the present methods variety of side effects may be treated, including, but not limited to organ system damage, nausea, vomiting, and hair loss. Examples of organ system damage include damage to the urinary system, the digestive system, the nervous system, the auditory system, the circulatory system, the endocrine system, the excretory system, the skeletal system, the respiratory system, the reproductive system, the muscular system, the lymphatic system, and the integumentary system. In some embodiments, the organ system is the urinary system and the urinary system damage may include damage to one or more kidneys.

Similarly, the methods encompass a variety of toxic medical therapies, including, but not limited to, chemotherapy, radiotherapy, and other therapies involving the administration of an agent that is capable of producing toxicity in normal tissues and/or non-target tissues (i.e., tissues that are not targeted for the therapeutic effect of the toxic medical therapy). toxic medical therapy comprises administration of an agent selected from the group consisting of mechlorethamine, cyclophosphamide, chlorambucil, carboplatin, oxaliplatin, cisplatin, azathioprine, mercaptopurine, vinca alkaloids, etoposide, teniposide, paclitaxel, docetaxel, irinotecan, topotecan, amsacrine, trastuzumab, cetuximab, rituximab, bevacizumab, dexamethasone, finasteride, aromatase inhibitors, tamoxifen, goserelin, antibiotics, contrast agents, NSAIDS, COX-2 inhibitors, ACE inhibitors, ARBs, and lithium. In some embodiments, the toxic medical therapy is chemotherapy comprising administration of cisplatin.

The effective amount of the nitrated lipid administered to the subject may vary. In some aspects, the effective amount is that which prevents the subject from experiencing any of the disclosed side effects with any of the disclosed toxic medical therapies. In other aspects, the effective amount is an amount that reduces or eliminates the subject's side effects relative to the subject's side effects prior to administration of the nitrated lipid.

The methods disclosed herein may further comprise administrating a variety of therapeutic agents useful in the treatment of the underlying condition, disease, or disorder giving rise to any of the toxic medical therapies disclosed herein.

BRIEF DESCRIPTION OF THE DRAWINGS

FIG. 1. Shown are plasma concentrations of BUN in mice under the conditions indicated. N=5-6. Data are mean±SE. B6129S2/J mice (male, 3-4-mo-old) received vehicle (Control) or a single i.p. injection of cisplatin alone (20 mg/kg in saline). After 20 min, the cisplatin group was randomly divided to receive an i.p injection of OA-NO2 (400 mg/kg in ethanol) or an equivalent amount of ethanol at 6-h intervals for 48 h. The results show that nitrated fatty acid OA-NO2 improves renal function in a mouse model of cisplatin-induced toxicity.

FIG. 6. Effects of nitrated fatty acid OA-NO2 on cisplatin-induced apoptosis in vivo and in vitro. A), Caspase activity in the mouse kidney. N=5-6 in each group. B), Caspase activity in cultured human proximal tubular cells (HK2). Following pretreatment for 1 h with vehicle or 1.5 µM OA-NO2, the cells were exposed for 24 h to 1 µM cisplatin. N=3 in each group. Data are mean±SE.

DETAILED DESCRIPTION

The following terms are used throughout as defined below.

"Treat" means to alleviate, in whole or in part, symptoms associated with a condition or disorder (e.g., disease), or halt of further progression or worsening of those symptoms, or prevention or prophylaxis of the condition or disorder. Similarly, as used herein, an "effective amount" of a compound disclosed herein refers to an amount of the compound that alleviates, in whole or in part, symptoms associated with a condition or disorder, or halts further progression or worsening of those symptoms, or prevents or provides prophylaxis for the disease or disorder. For example, in treating a side effect of a toxic medical treatment, the prevention of, reduction of, or elimination of the side effect are examples of desirable treatment results. Finally, treating does not necessarily occur by administration of one dose of the compound, but often occurs upon administration of a series of doses. Thus, an effective amount, an amount sufficient to alleviate, or an amount sufficient to treat a disease, disorder, or condition may be administered in one or more administrations.

The methods disclosed herein comprise administration of a nitrated lipid. Nitrated lipids are lipids comprising at least one nitro ($NO_2$) group covalently bonded to the lipid. The methods disclosed herein encompass administration of a single type of nitrated lipid or a mixture of two or more different types of nitrated lipids. By way of example, one type of nitrated lipid is 9-nitro-9-cis-octadecenoic acid. Thus, "type" identifies the compound by lipid, stereochemistry, and number and position of $NO_2$ groups.

Nitrated lipids include nitrated fatty acids or esters thereof. A fatty acid is a substituted or unsubstituted alkyl or alkenyl having a terminal COOH group. In some embodiments, the alkyl or alkenyl is a $C_8$-$C_{24}$ alkyl or alkenyl. A wide variety of fatty acids may be used, including, but not limited to monounsaturated fatty acids and polyunsaturated fatty acids. In some embodiments, the monounsaturated fatty acid is oleic acid. In some embodiments, the oleic acid is 9-nitrooleic acid, 10-nitrooleic acid, or combinations thereof. An ester of a fatty acid is a substituted or unsubstituted alkyl or alkenyl having a terminal COOR group. In some embodiments, the alkyl or alkenyl is a $C_8$-$C_{24}$ alkyl or alkenyl. R may include, but is not limited to, a $C_{1-8}$ alkyl or glyceryl.

Nitrated lipids may be synthesized according to known procedures. For example, U.S. Patent Publication No. 2007/0232579 (incorporated herein by reference in its entirety) discloses a procedure comprising the steps of reacting a lipid with a mercuric salt, a selenium compound, and a nitrating compound to produce a first intermediate and reacting the first intermediate with an oxidant. Useful mercuric salts, selenium compounds, nitrating compounds, oxidants, relative amounts of reactants, and reaction conditions are also disclosed in U.S. Patent Publication No. 2007/0232579. Such synthetic procedures may provide mixtures of two or more types of nitrated lipids which may be separated or purified by techniques known in the art, if desired.

The lipids described above may be obtained from a variety of sources. For example, lipids may be commercially available or may be obtained from natural sources. Plant oils, including, but not limited to olive oil, linseed oil, flaxseed oil, rapeseed oil, and perilla oil are possible natural sources of fatty acid lipids. Fish oils or other marine oils are other possible sources of fatty acids. Nitrated lipids present in any of these or other natural sources may be extracted and/or purified for use in the methods disclosed herein.

The disclosed methods involve treatment of a side effect of a toxic medical therapy. A variety of side effects may be treated, including, but not limited to organ system damage, nausea, vomiting, and hair loss. By organ system, it is meant a group of related organs. By way of example only, the urinary system is an organ system including the kidneys, the ureters, the bladder, and the urethra. Other examples of organ systems include, but are not limited to, the digestive system, the nervous system, the auditory system, the circulatory system, the endocrine system, the excretory system, the skeletal system, the respiratory system, the reproductive system, the muscular system, the lymphatic system, and the integumentary system. "Organ system damage" refers to damage to one or more of the organs making up the organ system as a result of a toxic medical therapy. Organ damage may include, but is not limited to, oxidative stress to the organ, and necrosis or apoptosis of organ cells.

These examples of organ damage and others may be readily identified using well-known pathological techniques. By way of example only, kidney damage may be identified by examining the overall renal morphology, the dilation of renal tubules, and the appearance of protein cast. Organ damage may also be identified by measuring certain biomarkers of organ damage in a subject. Useful biomarkers include, but are not limited to biological substances or activities that provide a marker of organ dysfunction, oxidative stress, necrosis or apoptosis. By way of example only, a biomarker of organ dysfunction includes, but is not limited to the rise of plasma creatinine and BUN for renal dysfunction, and the rise of serum aspartate aminotransferase (AST) and alanine aminotransferase (ALT) for hepatic dysfunction. Biomarkers of oxidative stress include, but are not limited to, the NADPH oxidase subunits p47$^{phox}$ and gp91$^{phox}$ and thiobarbituric acid-reactive substances (TBARS).

A biomarker of apoptosis includes, but is not limited to, the activity of caspase 3, 6, and 9. Another biomarker of organ damage is myeloperoxidase, MPO. An increase in the level of MPO, BUN, AST, ALT, TBARS, p47$^{phox}$ or gp91$^{phox}$ in a subject or an increase in the activity of caspase 3,6, and 9 in the subject may provide an indication of organ damage.

The disclosed methods encompass a variety of toxic medical therapies. By toxic medical therapy it is meant a medical therapy that involves administration of an agent that is capable of producing toxicity in normal tissues. The agent may be chemical or physical. Chemical agents include, but are not limited to, alkylating agents, anti-metabolites, alkaloids and terpenes, topoisomerase inhibitors, antibiotics, monoclonal antibodies, tyrosine kinase inhibitors, and hormones. Examples of alkylating agents include, but are not limited to, cisplatin, mechlorethamine, cyclophosphamide, chlorambucil, carboplatin, and oxaliplatin. Examples of anti-metabolites include, but are not limited to azathioprine, mercaptopurine, and other purine and pyrimidine analogues. Examples of alkaloids and terpenes include, but are not limited to, vinca alkaloids, etoposide, teniposide, paclitaxel, and docetaxel. Examples of topoisomerase inhibitors include, but are not limited to, irinotecan, topotecan, and amsacrine. Examples of monoclonal antibodies include, but are not limited to, trastuzumab, cetuximab, rituximab, and bevacizumab. Examples of hormones include, but are not limited to, steroids such as dexamethasone, finasteride, aromatase inhibitors, tamoxifen, and goserelin. Other examples of chemical agents include, but are not limited to, contrast agents, NSAIDS, COX-2 inhibitors, ACE inhibitors, ARBs, and lithium. An example of a physical agent includes, but is not limited to, radiation. By way of example only, the radiation may be ionizing radiation or laser radiation.

In the disclosed methods, the nitrated lipids are administered to a subject in an effective amount. An effective amount is an amount that 1) prevents the subject from experiencing any of the disclosed side effects associated with any of the disclosed toxic medical therapies; 2) reduces the subject's side effects relative to the subject's side effects prior to administration of the nitrated lipid; and/or eliminates the subject's side effects relative to the subject's side effects prior to administration of the nitrated lipid. By way of example only, in some embodiments, the side effect is urinary system damage comprising damage to one or more kidneys. In this illustrative example, the effective amount is an amount that prevents, reduces, or eliminates the damage to the kidneys. The damage to the kidneys may include, but is not limited to, any of the types of damage described above.

As is understood by those of skill in the art, specific effective amounts of the nitrated lipids to be administered will vary depending upon a variety of factors, e.g., the condition to be treated, the age, body weight, general health, sex, and diet of the subject, the dose intervals, and the administration route. In some embodiments, the effective amount of the nitrated lipid ranges from about 1 µg per day to about 1 g per day, from about 1 mg per day to about 500 mg per day, from about 1 mg per day to about 100 mg per day, or from about 2 mg per day to about 10 mg per day.

Any of the nitrated lipids disclosed herein may be administered to the subject alone or in combination with one or more other therapeutic agents. By "administered in combination," it is meant that the nitrated lipids and the therapeutic agents may be administered as a single composition, simultaneously as separate doses, or sequentially. Sequential administration refers to administering the nitrated lipids and at least one therapeutic agent either before or after the other. A variety of therapeutic agents may be used, including, but not limited to, those useful in the treatment of the underlying condition, disease, or disorder giving rise to any of the toxic medical therapies disclosed herein.

The nitrated lipids may be administered to a subject via any number of pharmaceutical formulations and administration routes. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. The formulations may be delivered to the subject by various routes of administration, e.g., by topical administration, transdermal administration, oral administration, by nasal administration, rectal administration, subcutaneous injection, intravenous injection, intramuscular injection, or intraperitoneal injection. Any of the formulations, delivery methods, and pharmaceutically acceptable additives, carriers, and excipients disclosed in U.S. Patent Publication No. 2007/0232579 may also be used with the methods described herein. Another possible route of administration includes incorporating the nitrated lipid into various food products. Food products, include, but are not limited to butter, margarine, vegetable oils, and the like.

The subjects of the disclosed methods include any animal that can benefit from the administration of a nitrated lipid. In some embodiments, the subject is a mammal, e.g., a human, a primate, a dog, a cat, a horse, a cow, a pig, or a rodent, e.g., a rat or mouse. Typically, the mammal is a human. In some aspects, the subject is undergoing or has undergone any of the disclosed toxic medical therapies. Such subjects may or may not actually be experiencing any of the disclosed side effects. In other aspects, the subject has not yet undergone the toxic medical therapy, but is susceptible to any of the disclosed side effects because of an imminent toxic medical therapy.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

The present invention, thus generally described, will be understood more readily by reference to the following examples, which are provided by way of illustration and are not intended to be limiting of the present invention.

EXAMPLES

Materials and Methods

Animals.

Male 3-4-month-old B6129SF2/J mice were from Jackson Laboratories (Bar Harbor, Md.). All animals were housed in an air-conditioned room with a 12-hour light/dark cycle. All procedures and protocols were in accordance with guidelines set by the Laboratory Animal Care Committee at the University of Utah.

Materials.

9-Nitrooleic acid and 10-nitrooleic acid are two regioisomers of nitrooleic acid ($OA-NO_2$), which are formed by nitration of oleic acid in approximately equal proportions in vivo. The two compounds were purchased from Cayman Chemicals (Ann Arbor, Mich.) (9-nitrooleic acid: Cat#10008042; 10-nitrooleic acid: Cat#10008043) and used as an 1:1 mixture of the isomers.

Protocols for Animal Experiments

Protocol for testing effects of OA-NO2 on cisplatin-induced toxicity in B6129SF2/J mice. B6129S2/J mice (male, 3-4-mo-old) received vehicle (saline) or a single i.p. (intraperitoneal) injection of cisplatin alone (20 mg/kg in saline). After 20 minutes, the cisplatin group was randomly divided to receive an i.p injection of OA-NO2 (400 mg/kg in ethanol) or an equivalent amount of ethanol at 6-hour intervals for 48 hours. The control group also received an i.p. injection of the equivalent amount of ethanol at the same frequencies. At the end of the experiments, under isoflurane anesthesia, blood was withdrawn from the vena cava using 1 cc insulin syringe and kidneys were harvested for analysis of morphology and gene expression.

Example

Figure 1:
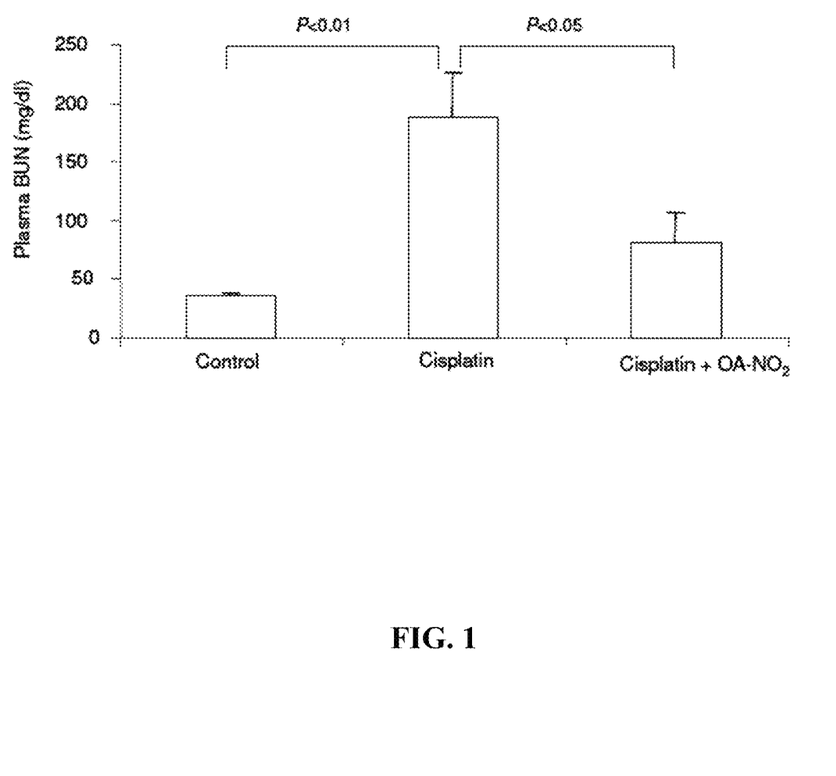
Figure 2:
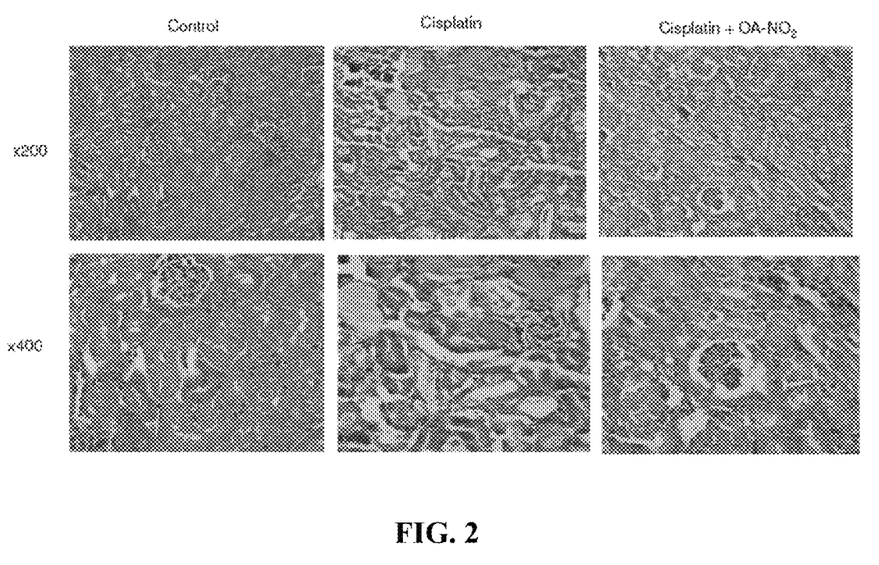
FIG. 2. The nitrated fatty acid OA-NO2 improves renal morphology in a mouse model of cisplatin-induced toxicity. Shown are representative images of renal morphology at ×200 and ×400 magnifications.
Figure 3:
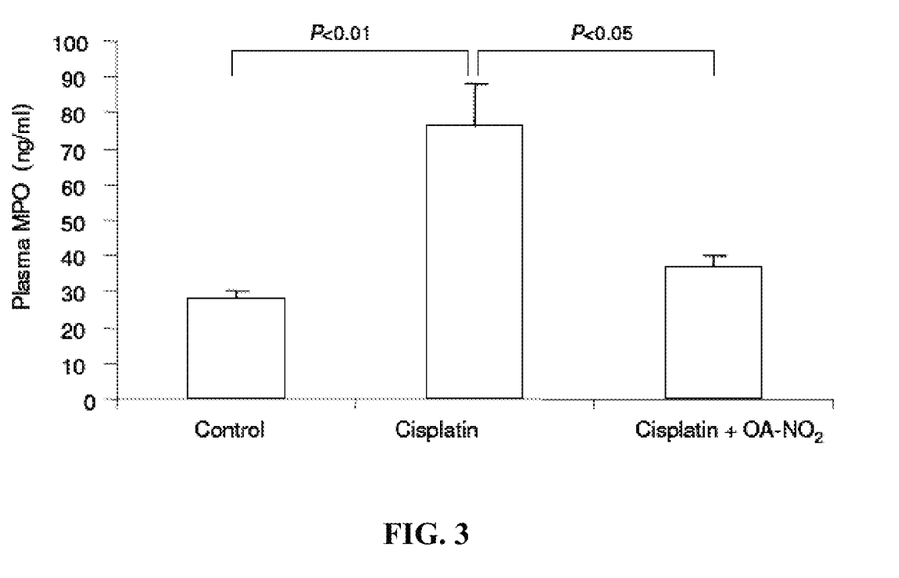
FIG. 3. The nitrated fatty acid OA-NO2 reduces plasma myeloperoxidase (MPO) in cisplatin treated mice. MPO concentrations are determined by EIA. N=5-6. Data are mean±SE.
Figure 4:
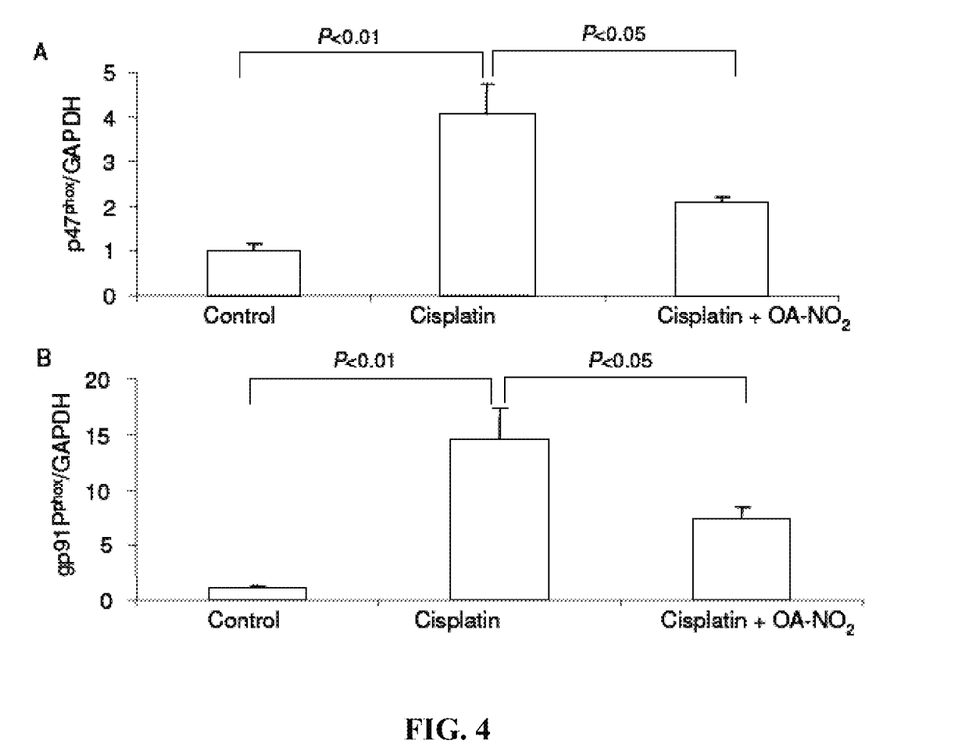
FIG. 4. Real time RT-PCR analysis of p47$^{phox}$ (A), gp91$^{phox}$ (B) in control mice and mice treated with cisplatin alone or in combination with OA-NO2. N=5-6 in each group. Data are mean±SE.
Figure 5:
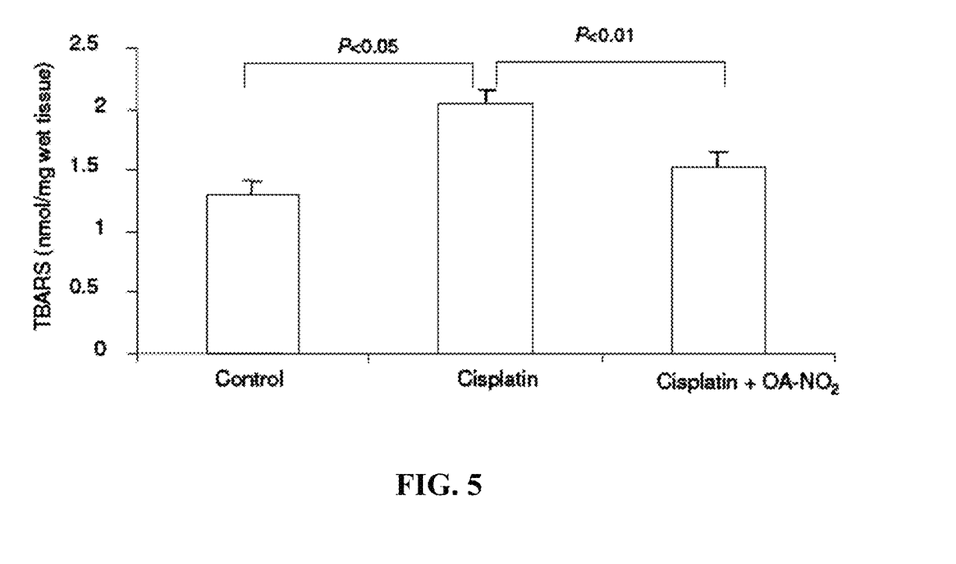
FIG. 5. Kidney TBARS in control mice and mice treated with cisplatin alone or in combination with OA-NO2. N=5-6 in each group. Data are mean±SE.
Figure 6:
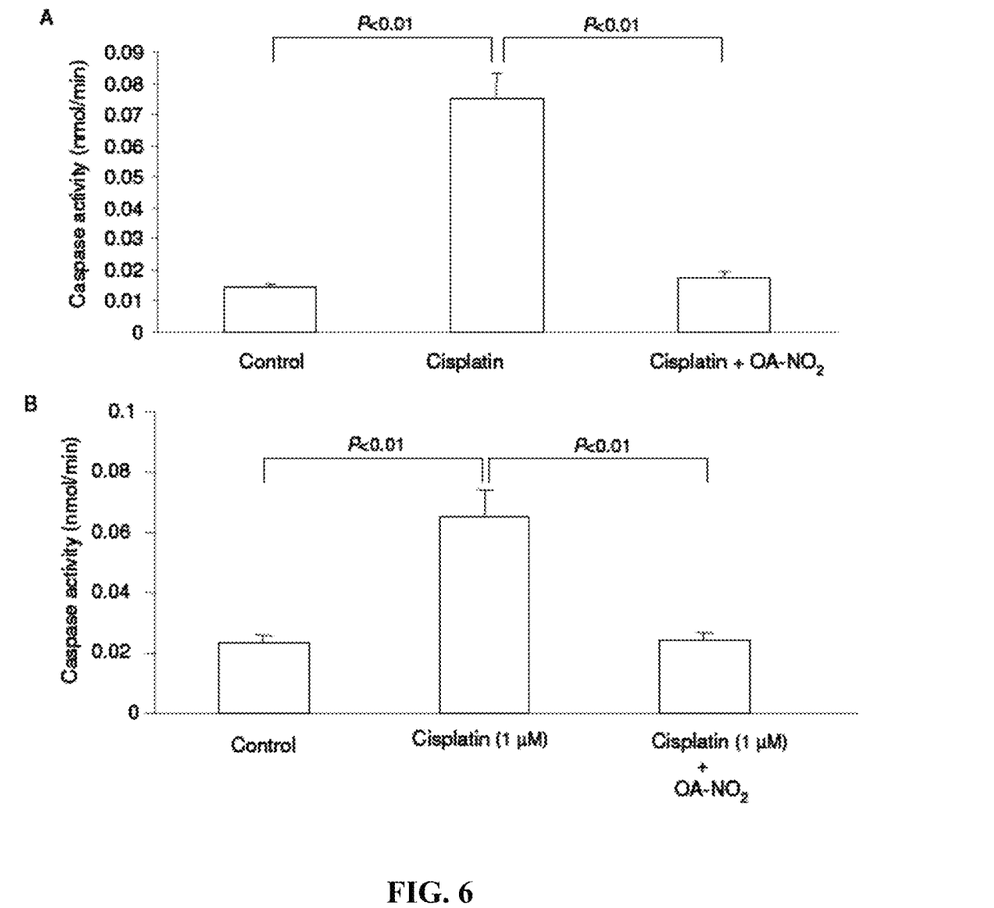

Evaluation of the Therapeutic Potential for Using Nitrated Fatty Acid $OA-NO_2$ in Managing Chemotherapy-Related Toxicity A single dose of i.p. injection of cisplatin induced renal dysfunction as indicated by the marked rise in plasma BUN (FIG. 1), accompanied by severe renal histological abnormalities characterized by distortion of the overall renal morphology, dilation of renal tubules, and appearance of protein cast (FIG. 2). In a sharp contrast, posttreatment with OA-NO2 markedly attenuated these functional and pathological changes (FIGS. 1 and 2). Cisplatin treatment induced increases in plasma level of MPO (marker of neutrophil infiltration) (FIG. 3), kidney expression of NADPH oxidase subunits $p47^{phox}$ and $gp91^{phox}$ (major superoxide generating enzyme) (FIG. 4), kidney thiobarbituric acid-reactive substances (TBARS, index of oxidative stress) (FIG. 5), and activity of caspase (index of apoptosis) (FIG. 6A), all of which were attenuated or completely corrected by OA-NO2. In cultured human proximal tubular cells (HK2), exposure to 1.0 µM cisplatin induced a 3-fold increase in caspase activity that was almost completely normalized by OA-NO2 (FIG. 6B).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of treating renal system damage in a subject comprising administering to the subject an effective amount of a nitrated fatty acid;
    wherein the renal system damage is selected from a group consisting of nephrotoxicity, distortion of the overall renal morphology, dilation of renal tubules, appearance of protein cast, oxidative stress, necrosis, and apoptosis of organ cells.

2. The method of claim 1, wherein the nitrated fatty acid is a monounsaturated fatty acid or a polyunsaturated fatty acid.

3. The method of claim 1, wherein the nitrated fatty acid is nitro-oleic-acid.

4. The method of claim 1, wherein the nitrated fatty acid is selected from the group consisting of 9-nitrooleic acid, 10-nitrooleic acid, and combinations thereof.

5. The method of claim 1, wherein the effective amount is from about 1 milligram per day to about 500 milligrams per day.

* * * * *

UNITED STATES PATENT AND TRADEMARK OFFICE
CERTIFICATE OF CORRECTION

PATENT NO. : 9,585,855 B2
APPLICATION NO. : 14/205108
DATED : March 7, 2017
INVENTOR(S) : Tianxin Yang It is certified that error appears in the above-identified patent and that said Letters Patent is hereby corrected as shown below:

In the Specification

Column 1, Line 19, after "STATEMENT OF GOVERNMENT RIGHTS," delete "This invention was made with government Support under RO-1 HL079453 and RO-1 DK 066592 by the National Institutes of Health. The government has certain rights to this invention" and replace it with:
--This invention was made with government support under Grant Numbers R01 DK066592 & HL079453 awarded by the National Institutes of Health. The government has certain rights in the invention.--

Signed and Sealed this
Nineteenth Day of May, 2020

Andrei Iancu
*Director of the United States Patent and Trademark Office*